(12) United States Patent
Greenspan et al.

(10) Patent No.: US 7,888,313 B2
(45) Date of Patent: Feb. 15, 2011

(54) COMPOSITION FOR TREATING A FIBROTIC DISORDER COMPRISING AN INHIBITOR OF A BMP-1-LIKE PROTEIN

(75) Inventors: Daniel S Greenspan, Madison, WI (US); Yue Zhang, Madison, WI (US); Gaoxiang Ge, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 210 days.

(21) Appl. No.: 11/842,527

(22) Filed: Aug. 21, 2007

(65) Prior Publication Data
US 2008/0085863 A1  Apr. 10, 2008

Related U.S. Application Data

(60) Provisional application No. 60/839,019, filed on Aug. 21, 2006.

(51) Int. Cl.
  *A61K 38/00* (2006.01)
  *A61K 38/55* (2006.01)
  *A61K 38/16* (2006.01)
  *C07K 14/00* (2006.01)
  *C07K 14/81* (2006.01)
  *C12N 15/62* (2006.01)

(52) U.S. Cl. .................. 514/1.1; 514/9.4; 514/20.1; 514/21.2; 530/350; 435/69.7

(58) Field of Classification Search .............. None
See application file for complete search history.

(56) References Cited

FOREIGN PATENT DOCUMENTS
WO        91/03557 A    3/1991

OTHER PUBLICATIONS
Fisher et al. (1991, J. Bio. Chem. 266:14371-14377).*

Baker A, et al., "Metalloproteinase inhibitors: biological actions and therapeutic opportunities," J. Cell Sci. 115:3719-3727 (2002).
Enghild J, et al., "Interaction of human rheumatoid synovial collagenase (matrix metalloproteinase 1) and stromelysin (matrix metalloproteinase 3) with human alpha 2-macroglobulin and chicken ovostatin. Binding kinetics and identification of matrix metalloproteinase cleavage sites," J. Biol. Chem. 264:8779-8785 (1989).
Ge G & Greenspan D, "Developmental roles of the BMP1/TLD metalloproteinases," Birth Defects Res. (Part C) 78:47-68 (2006).
Hopkins D, et al., "The bone morphogenetic protein 1/Tolloid-like metalloproteinases," Matrix Biol. 26:508-523 (2007).
Lee H, et al., "Embryonic dorsal-ventral signaling: secreted frizzled-related proteins as inhibitors of tolloid proteinases," Cell 124:147-159 (2006).
Scott I, et al., "Bone morphogenetic protein-1 processes probiglycan," J. Biol. Chem. 275:30504-30511 (2000).
Tiggelman A, et al., "Transforming growth factor-beta-induced collagen synthesis by human liver myofibroblasts is inhibited by alpha2-macroglobulin," J. Hepatol. 26:1220-1228 (1997).
Tortorella M, et al., "Alpha2-macroglobulin is a novel substrate for ADAMTS-4 and ADAMTS-5 and represents an endogenous inhibitor of these enzymes," J. Biol. Chem. 279:17554-17561 (2004).
Van Rompaey L, et al., "Inhibition of intracellular proteolytic processing of soluble proproteins by an engineered alpha 2-macroglobulin containing a furin recognition sequence in the bait region," Biochem. J. 326:507-514 (1997).
Veitch D, et al., "Mammalian tolloid metalloproteinase, and not matrix metalloprotease 2 or membrane type 1 metalloprotease, processes laminin-5 in keratinocytes and skin," J. Biol. Chem. 278:15661-15668 (2003).
Zhang Y, et al., "Inhibition of bone morphogenetic protein 1 by native and altered forms of α2-macroglobulin," J. Biol. Chem. 281:39096-39104 (2006).

* cited by examiner

*Primary Examiner*—Elizabeth C. Kemmerer
(74) *Attorney, Agent, or Firm*—Quarles & Brady LLP

(57) ABSTRACT

$\alpha_2$-macroglobulin-related agents for treating or preventing a fibrotic disorder associated with fibrillogenesis are disclosed along with methods for using the agents, as well as methods for producing agents suited for use in the disclosed methods for treating or preventing a fibrotic disorder.

9 Claims, 10 Drawing Sheets

FIG. 2B  FIG. 2C

WB: α FLAG

WB: α α₂M

FIG. 6A
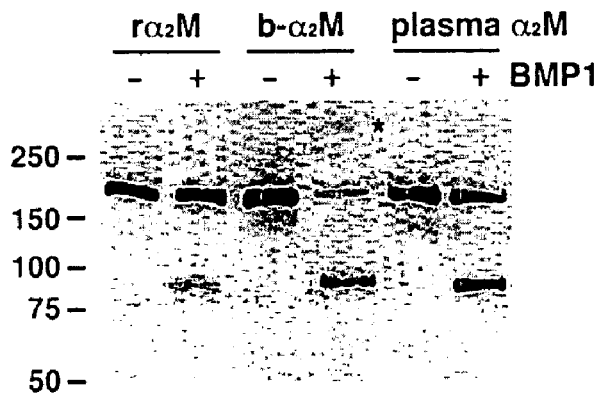
FIG. 6D
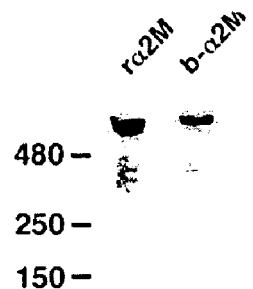
FIG. 6B
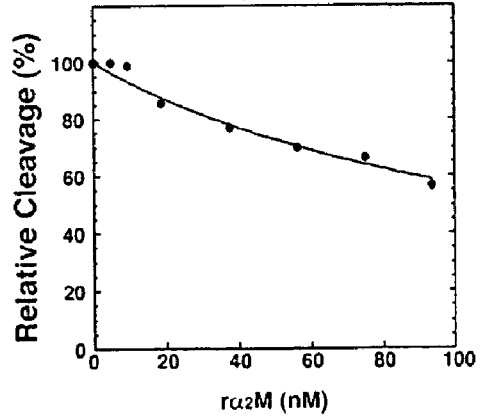
FIG. 6E
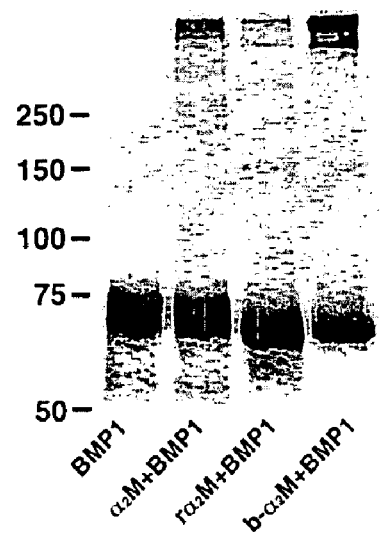
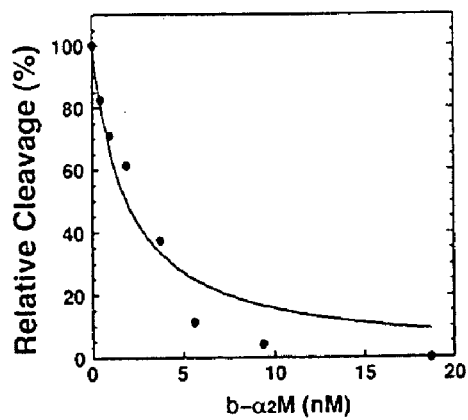
FIG. 6C

COMPOSITION FOR TREATING A FIBROTIC DISORDER COMPRISING AN INHIBITOR OF A BMP-1-LIKE PROTEIN

CROSS-REFERENCE TO RELATED APPLICATIONS

This application claims the benefit of U.S. Provisional Patent Application No. 60/839,019, filed Aug. 21, 2006, incorporated herein by reference as if set forth in its entirety.

STATEMENT REGARDING FEDERALLY SPONSORED RESEARCH OR DEVELOPMENT

This invention was made with United States government support awarded by the following agencies: NIH GM063471, GM071679 and AR047746. The United States government has certain rights in this invention.

BACKGROUND $\alpha_2$-macroglobulin ($\alpha_2$M) is a member of an $\alpha$-macroglobulin family of proteins found in plasma and egg whites of a broad range of animal species. $\alpha_2$M is present in human plasma at relatively high levels (i.e., 2-4 mg/ml) and is produced by several cell types, such as hepatocytes, lung fibroblasts, macrophages, astrocytes and tumor cells. Borth W, "Alpha 2-macroglobulin. A multifunctional binding and targeting protein with possible roles in immunity and autoimmunity," Ann. N.Y. Acad. Sci. 737:267-272 (1994), incorporated herein by reference as if set forth in its entirety.

$\alpha_2$M was initially thought to function in plasma and tissue as a humoral defense barrier that binds host or foreign peptides and particles via exposed 39 amino acid "bait regions" present on each of four identical 185 kDa subunits. Each bait region contains sites at which various proteinases, or other nucleophiles, can cleave the subunits, thereby activating $\alpha_2$M by changing the subunit conformation, and exposing a highly reactive internal thioester. Borth W, "Alpha 2-macroglobulin, a multifunctional binding protein with targeting characteristics," FASEB J. 6:3345-3353 (1992); and Sottrup-Jensen L, "Alpha-macroglobulins: structure, shape, and mechanism of proteinase complex formation," J. Biol. Chem. 264:11539-11542 (1989). The thioester covalently binds and entraps the proteinase or nucleophile, inhibiting further activity by steric hindrance. For example, $\alpha_2$M inhibits metalloproteinases belonging to a disintegrin and metalloproteinase with thrombospondin motifs (ADAMTS) family, see Tortorella M, et al., "Alpha 2-macroglobulin is a novel substrate for ADAMTS-4 and ADAMTS-5 and represents an endogenous inhibitor of these enzymes," J. Biol. Chem. 279:17554-17561 (2004), but was previously reported that it does not inhibit proteinases with astacin-like protease domains, see Baker A, et al., "Metalloproteinase inhibitors: biological actions and therapeutic opportunities," J. Cell Sci. 115:3719-3727 (2002).

Activated $\alpha_2$M is also a targeting carrier for cytokines or growth factors (e.g., TGF-$\beta$, PDGF; IL-1$\beta$, basic FGF and NGF) involved in modulating biological responses of various cell types. The cytokine or growth factor dissociates either on the cell surface of a cell expressing the low-density lipoprotein receptor-related protein (LPR) or in an endocytic compartment within the cell expressing the LPR. Activated $\alpha_2$M binds to LRP, which results in rapid clearance of $\alpha_2$M-proteinase complexes from the plasma or extracellular space for subsequent catabolism. In addition, $\alpha_2$M functions as a protective factor against many pathogens by binding to certain peptides (e.g. toxins or cell surface proteins) of some parasites, bacteria and viruses.

Bone morphogenetic protein-1 (BMP-1) is a prototype of a subgroup of structurally similar, secreted metalloproteinases having an astacin-like protease domain, CUB protein-protein interaction domains and EGF motifs. Bond J & Benyon R, "The astacin family of metalloendopeptidases," Protein Sci. 4:1247-1261 (1995). In mammals, members of this subgroup proteolytically cleave precursors into mature, extracellular matrix-(ECM) forming proteins. Members of this subgroup also activate some members of the TGF-$\beta$ superfamily in a broad range of species by cleaving extracellular protein antagonists. Thus, mammalian BMP-1-like proteinases (i.e., BMP-1, mammalian Tolloid (mTLD) and mammalian Tolloid-like 1 and 2 (mTLL-1 and mTLL-2, respectively)) are likely to be involved in forming ECM and in signaling by certain TGF-$\beta$-like molecules in morphogenetic events and homeostasis.

BMP-1 and Tolloid-like proteinases have a distinct protein domain, structure that includes (starting at the N-terminus) a signal peptide (for secretion), a prodomain (that must be cleaved to activate the proteinase), a conserved protease domain found in the astacin M12A family of metzincin metalloproteases, and then a number of CUB and EGF-like protein-protein interaction domains. See Ge G & Greenspan D, "Developmental roles of the BMP1/TLD metalloproteinases," Birth Defects Res. (Part C) 78:47-68 (2006); and Hopkins D, et al., "The bone morphogenetic protein 1/Tolloid-like metalloproteinases," Matrix Biol. (Epub ahead of print, May 18, 2007), each of which is incorporated herein by reference as if set forth in its entirety. These proteinases play diverse roles in morphogenetic events, via biosynthetic cleavage of precursors into mature functional proteins involved in formation of the ECM, and via activation of certain members of the TGF$\beta$ superfamily of growth factors. Greenspan D, "Biosynthetic processing of collagen molecules," Top. Curr. Chem. 247:149-183 (2005).

In particular, BMP-1-like proteinases (1) process type I-III procollagen C-propeptides to yield the major fibrous components of ECM; (2) cleave a zymogen to produce active lysyl oxidase enzyme that catalyzes covalent cross-linking in collagen fibers; and (3) process procollagen N-propeptides, and in some cases C-propeptides, of the minor fibrillar collagen types V and XI. Ge G, et al., "Bone morphogenetic protein-1/tolloid-related metalloproteinases process osteoglycin and enhance its ability to regulate collagen fibrillogenesis," J. Biol. Chem. 279:41626-41633 (2004). The latter are incorporated into growing fibrils of collagen types I and II, respectively, and appear to control the geometries of the resulting heterotypic fibrils.

Because BMP-1-like proteinases provide most, if not all procollagen C-proteinase (pCP) activity in vivo, and because C-propeptide removal is essential for collagen fibrillogenesis, the BMP-1-like proteinases are attractive targets for therapeutic interventions where inhibition of collagen fibrillogenesis is desirable. Although the formation of collagen fibrils is essential to morphogenesis and to healing of wounds and bone fractures in the adult, excessive formation of fibrous collagenous ECM causes much morbidity in the general population. These conditions include keloids (excessive skin scarring), surgical adhesions, and deep-seated fibroses of organs including lungs, liver and kidneys. The deep-seated fibroses are particularly ominous, as the replacement of parenchymal tissue by scar tissue composed essentially of fibrous, collagenous ECM destroys organ function.

Accordingly, there is a need for new methods and compositions for treating fibrotic disorders, particularly those that inhibit the activities of BMP-1-like proteinases.

BRIEF SUMMARY

In a first aspect, the present invention is summarized as a method of inhibiting a BMP-1-like proteinase in a human or non-human animal experiencing or susceptible to a fibrotic disorder caused by the BMP-1-like proteinase that includes administering to the animal an amount of an inhibitor of a BMP-1-like proteinase effective to reduce BMP-1-like proteinase activity in the animal, where the reduction is characterized by a reduction in severity or occurrence of the fibrotic disorder.

In some embodiments of the first aspect, the administered inhibitor is natural or modified $\alpha_2M$, and in related embodiments the $\alpha_2M$ is modified-relative to natural $\alpha_2M$ in that in place of a native bait region, a bait region of probiglycan, a small leucine-rich proteoglycan precursor, is present.

In a second aspect, the present invention is summarized as a method for engineering an inhibitor of a BMP-1-like proteinase from a naturally-occurring $\alpha_2M$ protein having a bait region that includes substituting the bait region with a bait region from a protein other than $\alpha_2M$ protein that is cleaved by BMP-1 to produce an engineered $\alpha_2M$ protein. In a related embodiment, the other protein can be a probiglycan, and can be a probiglycan from a human. The source of the naturally occurring $\alpha_2M$ protein is not critical, as long as the engineered protein contains a bait region that can be cleaved by a BMP-1-like proteinase.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention but rather to cover all modifications, equivalents and alternatives. Reference should therefore be made to the claims recited herein for interpreting the scope of the invention.

BRIEF DESCRIPTION OF THE DRAWINGS

The embodiments described herein will be better understood and features, aspects and advantages other than those set forth above will become apparent when consideration is given to the following detailed description thereof. Such detailed description makes reference to the following drawings, wherein:

FIG. 3 shows the time- and dose-dependent inhibition of BMP-1 procollagen C-proteinase activity by native and recombinant forms of $\alpha_2M$.

FIG. 5 shows that methylamine-treated $\alpha_2M$ is neither cleaved nor complexed by BMP-1 and does not inhibit cleavage of probiglycan by BMP-1.

FIG. 6 shows that substituting the probiglycan bait region sequences in place of the native α$_2$M bait region enhances α$_2$M inhibition of BMP-1~25-fold. (FIG. 6A) A Western blot probed with anti-α$_2$M is shown of plasma α$_2$M, or recombinant wild type α$_2$M (rα$_2$M) or mutant (b-α$_2$M) α$_2$M incubated in the presence (+) or absence (−) of BMP-1. (FIGS. 6B and 6C) 9.4 nM BMP-1 was preincubated with 0, 4.7, 9.4, 18.7, 37.5, 56.2, 75.0, or 93.7 nM wild type α$_2$M (FIG. 6B) or 0, 0.47, 0.94, 1.87, 3.75, 5.62, 9.4, or 18.7 nM b-α$_2$M (FIG. 6C) for 2 hours at 37° C., followed by incubation with 400 ng $^3$H-radiolabeled type I procollagen. Cleavage reaction samples were analyzed by SDS-PAGE on 5% gels, followed by scanning of autofluorograms, quantification of bands, using NIH Image software, and plotting of relative percent cleavage of substrate vs nM concentration of α$_2$M. Non-linear regression was performed using SigmaPlot. (FIG. 6D) A Western blot is shown of recombinant wild type (rα$_2$M) or mutant (b-α$_2$M) α$_2$M cross-linked with glutaraldehyde. (FIG. 6E) An autofluorogram shows the SDS-PAGE electrophoretic patterns of $^{35}$S-radiolabeled BMP-1 incubated alone, or in the presence of plasma α$_2$M (α$_2$M) or recombinant wild type α$_2$M (rα$_2$M) or mutant (b-α$_2$M) α$_2$M. Numbers to the left of the autofluorogram correspond to the positions and approximate sizes, in kDa, of molecular mass markers;

FIG. 7 shows that α$_2$M can inhibit procollagen processing by cells. FIG. 8 shows the relative conservation of amino acid residues flanking BMP-1 cleavage sites.

DESCRIPTION OF PREFERRED EMBODIMENTS

Figure 1:
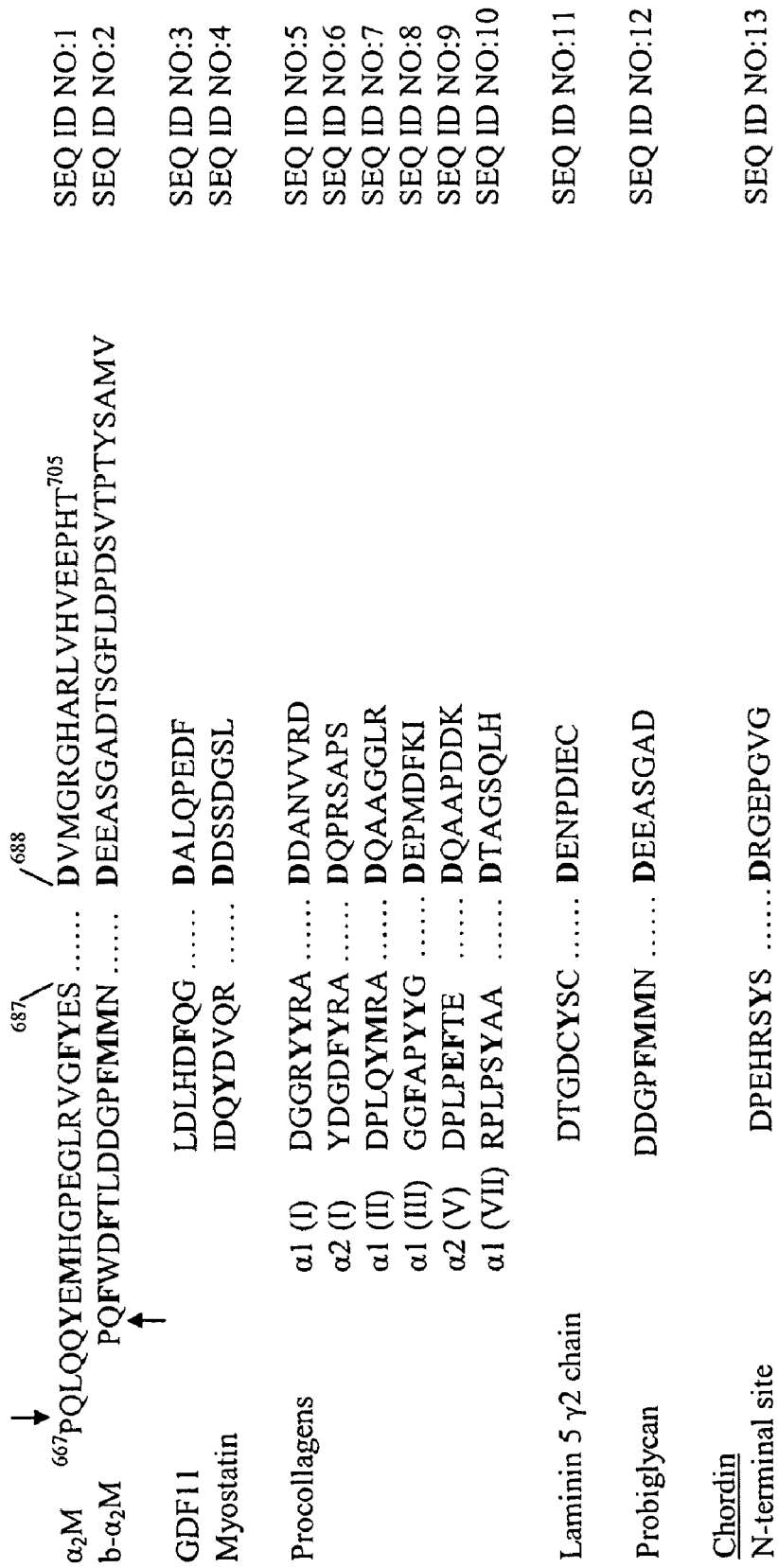
FIG. 1 shows $\alpha_2M$ as a candidate substrate for cleavage by BMP-1-like proteinases. The bait region from human $\alpha_2M$ (residues 667-705) is aligned with the cleavage sites of a number of protein substrates of BMP-1-like proteinases, including growth differentiation factor 11 (GDF-11), myostatin, procollagens I-III and the pro-$\alpha 2$(V) and pro-$\alpha 1$ (VII) procollagen chains, a $\gamma 2$ chain of laminin 5, probiglycan and an N-terminal cleavage site of chordin immediately beneath the $\alpha_2M$ sequence is the probiglycan sequence that substitutes for the native bait region in a mutant $\alpha_2M$ (b-$\alpha_2M$). Vertical arrows mark the sites of potential ADAMTS-2 cleavage sites in $\alpha_2M$ and b-$\alpha_2M$. Aspartate residues conserved at the P1' positions of the various scissile bonds are in boldface, as are aromatic side chains, previously noted NH$_2$-terminal to scissile bonds in many previously identified substrates of BMP-1-like proteinases. Phe$^{684}$, Tyr$^{685}$ and Asp$^{688}$ of the $\alpha_2M$ sequence are similarly presented in boldface.

Disclosed herein is a site for cleavage of α$_2$M by some astacin-like proteinases, particularly BMP-1. See also, Zhang Y, et al., "Inhibition of bone morphogenetic protein 1 by native and altered forms of alpha2-macroglobulin," J. Biol. Chem. 281:39096-39104 (2006), incorporated herein by reference as if set forth in its entirety. Cleavage at this site by BMP-1 results in formation of covalent complexes with cleaved α$_2$M and potent inhibition of BMP-1 proteolytic activities. Also, a modified α$_2$M, containing the probiglycan BMP-1 cleavage site in place of the native bait region, has enhanced ability to inhibit BMP-1 and to inhibit procollagen I processing by cells.

One inhibits a BMP-1-like proteinase such as BMP-1, mTLD, mTLL-1 or mTLL-2 in a human or non-human animal by administering an amount of an inhibitor of a BMP-1-like proteinase effective to reduce BMP-1-like proteinase activity in the animal. BMP-1-like proteinase activity is inhibited relative to pre-administration activity by at least 60%, alternatively by at least 75%, alternatively by at least 80%, alternatively by at least 85% and alternatively by at least 90%. The route of delivery varies depending upon the type of disorder being treated. That is, the inhibitor is administered topically for disorders such as keloids or for preventing excess scarring after cornea surgery or after other surgeries as well. Other routes of delivery include inhalation for pulmonary fibrosis. Furthermore, systemic delivery is contemplated for a surgical adhesion or for deep-seated fibroses of an organ. Preferred inhibitor delivery routes are topical and intravenous. The skilled artisan will appreciate the desirability of non-invasive administration of the agent. For topical delivery, creams, lotions or ointments comprising the inhibitor are a preferred delivery vehicle. For intravenous administration, the agent is provided in a pharmaceutically acceptable carrier, such as saline.

The inhibitor is natural or modified α$_2$M. As described further below, the modified α$_2$M is modified relative to natural α$_2$M in that in place of the native bait region, a bait region of probiglycan, a small leucine-rich proteoglycan precursor, is present. The number of doses a human or non-human animal receives, the time allowed between doses and the length of time the human or non-human animal receives a natural or modified α$_2$M can depend on the severity of the fibrotic disorder. Dosage level and the time between doses can be modified in accord with clinical assessment of the human or non-human animal.

It is contemplated that the methods described herein can be used with any fibrotic disorder, especially those disorders involving deposition of collagen I. Examples of fibrotic disorders include, but are not limited to, a keloid or other abnormal wound healing, a surgical adhesion or deep-seated fibroses of an organ.

Unless defined otherwise, all technical and scientific terms used herein have the same meaning as commonly understood by one of ordinary skill in the art to which the invention belongs. Although any methods and materials similar or equivalent to those described herein can be used in the practice or testing of the embodiments, the preferred methods and materials are now described.

As used herein, an "effective amount" refers to that concentration of $\alpha_2M$ or of a modified $\alpha_2M$ that is effective in attenuating fibrillogenesis and, hence, a fibrotic disorder.

As used herein, a "BMP-1-like proteinase" refers to a proteinase including, without limitation, BMP-1, mTLD, mTLL-1 and mTLL-2 that possesses an astacin-like protease domain, CUB protein-protein interaction domains and EGF motifs.

The invention embraced by the claims recited below will be more fully understood upon consideration of the following non-limiting Examples.

EXAMPLES

Example 1

Inhibition of BMP-1 by $\alpha_2M$

Methods:

Cleavage of $\alpha_2M$ by BMP-1: 200 nM Flag-tagged recombinant BMP-1, prepared and purified as previously described, was incubated overnight at 37° C. with 200 nM human $\alpha_2M$ (Sigma-Aldrich; St. Louis, Mo.) in 50 mM Tris-HCl, pH 7.5, 100 mM NaCl and 10 mM $CaCl_2$. Scott I, et al., "Mammalian BMP-1/Tolloid-related metalloproteinases, including novel family member-mammalian Tolloid-like 2, have differential enzymatic activities and distributions of expression relevant to patterning and skeletogenesis," Dev. Biol. 213:283-300 (1999). Subsequently, reaction proteins were analyzed by SDS-PAGE under reducing conditions on a 7.5% gel and staining with Coomassie Brilliant Blue R-250. For Western blot analysis, 320 nM BMP-1 was incubated with 200 nM $\alpha_2M$ at 37° C. overnight, and the samples were loaded on a 7.5% gels and separated by SDS-PAGE, under both nonreducing and reducing conditions. Separated proteins were transferred to polyvinylidene difluoride membranes and probed with a 1:5,000 dilution of anti-FLAG antibody (Sigma-Aldrich). Subsequently, membranes were incubated with a 1:25,000 dilution of goat anti-mouse IgG HRP conjugate as the secondary antibody.

For a dose-dependence study, $\alpha_2M$ was pre-incubated with BMP-1 for 2 hours at 37° C. The study of time-dependent inhibition of BMP-1 by $\alpha_2M$ indicates that complex formation between $\alpha_2M$ and BMP-1 is complete (reaches equilibrium) after 2 hours pre-incubation, under the conditions used. Thus, the rate of procollagen processing is proportional to the amount of active BMP-1 remaining uncomplexed to $\alpha_2M$.

Time-Dependent Inhibition of BMP-1 Cleavage of Probiglcyan by $\alpha_2M$: 15 ng BMP-1 (9.4 nM) was preincubated with or without 5 times the amount of $\alpha_2M$ (47.0 nM) in 50 mM Tris-HCl, pH 7.5, 100 mM NaCl and 10 mM $CaCl_2$ for 2 hours at 37° C. Subsequently, 450 ng probiglycan, prepared as previously described in Scott et al., was added to a final volume of 20 µl and incubated overnight. Scott I, et al., "Bone morphogenetic protein-1 processes probiglycan," J. Biol. Chem. 275:30504-30511 (2000). Cleavage reactions were quenched by adding 4 µl chondroitinase ABC (a mixture of 10 µl 0.01 U/µl protease-free chondroitinase ABC (Seikaguku Corp.; Tokyo, Japan), 40 µl 6× chondroitinase buffer (100 mM Tris-HCl, pH 8.0, 240 mM NaAc, 0.25 mM EDTA) and 10 µl 500 mM EDTA), followed by incubation at 37° C. for 4 hours. Samples were subjected to SDS-PAGE on a 10% gel and Western blot analysis was performed, using anti-probiglycan antibody LF51 at a 1:5,000 dilution, and a 1:25,000 dilution of goat-anti-rabbit IgG horse radish peroxidase (HRP) conjugate, as the secondary antibody.

Inactivation of $\alpha_2M$ by Methylamine: 1 mg/ml $\alpha_2M$ was incubated with 50 mM Tris-HCl, pH 7.1 in the presence or absence of 20 mM methylamine 20 hours, followed by dialysis against 50 mM Tris-HCl, pH 7.5, 100 mM NaCl. Both methylamine-treated and control $\alpha_2M$ samples were tested for ability to be cleaved by BMP-1 and for ability to inhibit BMP-1 cleavage of probiglycan.

Production of recombinant $\alpha_2M$: Human $\alpha_2M$ (NM_000014; SEQ ID NO:14 and SEQ ID NO:15) sequences were PCR-amplified from human placenta cDNA in three fragments. The following primers were used: fragment 1 (amino acids 24-416 of SEQ ID NO:15), 5'-GCTAGCAGACTA-CAAAGACGATGACGACAAGT-CAGTCTCTGGAAAACCGCAGTAT-3' (SEQ ID NO:16; forward) and 5'-CAGTAAGAGAGGTACCCATAAC-3' (SEQ ID NO:17; reverse); fragment 2 (amino acids 416-1052 of SEQ ID NO:15), 5'-GTTATGGGTACCTCTCGTTACTG-3' (SEQ ID NO:18; forward) and 5'-ATGTAGGCTCGAGCT-TGGGC-3' (SEQ ID NO:19; reverse); fragment 3 (amino acids 1052-1474 of SEQ ID NO:15), 5'-GCCCAAGCTC-GAGCCTACAT-3' (SEQ ID NO:20; forward) and 5-GCG-GCCGCTCAAGCATTTrCCAAGATCTTTGCTG-3' (SEQ ID NO: 21; reverse).

PCR products were assembled into the full-length $\alpha_2M$ sequence into pBlueScript II KS+ (Stratagene), and cloned downstream of (and adjoined via an NheI site to) BM40/SPARC signal peptide sequences, between the HindIII and NotI of the tetracycline-inducible expression vector pcDNA4/TO (Invitrogen Corp.; Carlsbad, Calif.). The resulting construct expresses full-length $\alpha_2M$, except that the native signal peptide is replaced by the BM40 signal peptide, for optimization of secretion. In addition, upon cleavage of the signal peptide, a FLAG epitope remains at the $NH_2$-terminus of $\alpha_2M$ sequences.

To generate mutant $\alpha_2M$, an MfeI site was introduced into the 5'-end of $\alpha_2M$ bait region sequences, without changing the encoded protein, via two-step PCR. Primers used were: primer 1: 5'-GATATGTACAGCTTCCTAGAGGA-3' (SEQ ID NO:22); primer 2: 5'-GTTGCAATTGTGGACA-CATTTTGGGTTTACGA-3' (SEQ ID NO:23); primer 3: 5'-TCCACAATTGCAACAGTATGAAATGCATGGACCT-3' (SEQ ID NO:24); and primer 4: 5'-CTTTCGTACG-GTCTCCGTGTGA-3' (SEQ ID NO:25). PCR amplicons of primer 1 and 2, 3 and 4 were then used as templates for PCR amplification using primers 1 and 4. The resulting amplicon was cloned between BsrG I and BsiW I sites in the $\alpha_2M$ sequence.

Biglycan sequences were PCR amplified with primers 5'-GAGAGAATTCTGGGACTTCACCCTGGACGA-3' (SEQ ID NO:26; forward) and 5'-GAAAGGTACCATG-GCGCTGTAGGTGGGTGT-3' (SEQ ID NO:27; reverse). The amplicon was then digested with EcoRI and KpnI, and cloned between MfeI and BsiWI sites in the modified $\alpha_2M$ sequences. In the resulting mutant $\alpha_2M$ (b-$\alpha_2M$) the sequences flanking the human probiglycan BMP-1 cleavage site substitute for the bait region (see FIG. 1).

293 T-REx cells (Invitrogen Corp.) were maintained in Dulbecco's Modified Eagle's medium (DMEM), with 5 µg/ml blasticidin and 10% fetal bovine serum (FBS). Cells at 80% confluence were transfected with 1 µg expression plasmid/35 mm culture dish using Lipofectamine (Invitrogen Corp.). After 48 hours, cells were selected in the same type of medium supplemented with 200 µg/ml Zeocin. Production of secreted $\alpha_2M$, upon induction with 1 µg/ml tetracycline, was detected via Western blot.

Confluent cells were washed twice with phosphate buffered saline (PBS) and incubated in serum-free DMEM 15 minutes at 37° C. Cells were then washed once with PBS, followed by addition of serum-free DMEM containing 1 µg/ml tetracycline, to induce protein expression, and 40 µg/ml soybean trypsin inhibitor. Conditioned medium was harvested every 24 hours, and protease inhibitors were added to final concentrations of 5 mM EDTA, 1 mM phenylmethylsulfonyl fluoride, 1 mM N-ethylmaleimide, and 1 mM p-aminobenzoic acid. Conditioned medium was centrifuged to remove debris and supernatants were stored at −70° C. FLAG-tagged $\alpha_2$M and b-$\alpha_2$M were affinity-purified from conditioned medium using an anti-FLAG M2 column (Sigma-Aldrich), following manufacturer's instructions.

Cross-linking: 6.9 nM recombinant $\alpha_2$M or b-$\alpha_2$M were incubated 5 minutes with 80 mM glutaraldehyde (Sigma) in PBS at room temperature. Cross-linking was terminated by adding glycine to a final concentration of 0.2 M. Samples were separated by SDS-PAGE on 4-15% acrylamide gradient gels and were subjected to immunoblotting.

Determination of $K_i$ Values and second-order Rate Constants for BMP-1-$\alpha_2$M Interactions: Confluent 293 T-Rex cells producing recombinant BMP-1 were washed twice with PBS, and incubated 15 minutes in serum-free, Cys/Met-free DMEM at 37° C. Cells were then washed once with PBS, followed by addition of serum-free DMEM containing 1 µg/ml tetracycline, to induce protein expression, 40 µg/ml soybean trypsin inhibitor and 60 µCi/ml Pro-Mix $^{35}$S cell labeling mix (Amersham). Conditioned medium was harvested every 24 hours, and protease inhibitors were added to final concentrations of 1 mM phenylmethylsulfonyl fluoride, 1 mM N-ethylmaleimide, and 1 mM p-aminobenzoic acid. Metabolically $^{35}$S-radiolabeled BMP-1 was affinity-purified from conditioned medium using an anti-FLAG M2 column (Sigma), following manufacturer's instructions.

40 nM $^{35}$S-labeled BMP-1 was incubated with 20, 40, 80, 160, and 240 nM plasma $\alpha_2$M, or recombinant wild type $\alpha_2$M or with 5, 10, 20, 40, and 80 nM b-$\alpha_2$M at 37° C. in 50 mM Tris-HCl, pH 7.5, 100 mM NaCl and 10 mM CaCl$_2$. Reactions were stopped at 10, 30, 60, 90 and 120 minutes (plasma $\alpha_2$M and recombinant wild type $\alpha_2$M), or at 2, 5, 10, 20 and 30 minutes (b-$\alpha_2$M) by adding. SDS-PAGE sample buffer and boiling 5 minutes at 95° C. Protein samples were separated on 7.5% acrylamide SDS-PAGE gels, which were then treated with EN$^3$HANCE (DuPont) and exposed to film. Percentages of BMP-1 incorporated into high molecular weight complexes were determined by densitometry and kinetic parameters were determined essentially via the method of Enghild J, et al, "Interaction of human rheumatoid synovial collagenase (matrix metalloproteinase 1) and stromelysin (matrix metalloproteinase 3) with human alpha 2-macroglobulin and chicken ovostatin. Binding kinetics and identification of matrix metalloproteinase cleavage sites," J. Biol. Chem. 264:8779-8785 (1989).

Inhibition of Collagen Processing by Cells: 2×10$^5$ MC-3T3-E1 cells were plated in a 24 well plate, allowed to attach overnight, and then treated with 50 µg/ml ascorbate in DMEM 10% FBS for 24 hours. Cells were washed twice with PBS, and incubated in serum-free DMEM 15 minutes at 37° C. Cells were then washed once with PBS, followed by addition of serum-free DMEM containing 50 µg/ml ascorbate, 40 µg/ml soybean trypsin inhibitor, and 20 nM $\alpha_2$M or b-$\alpha_2$M, or an equivalent volume of buffer (50 mM Tris-HCl, pH 7.5, 150 mM NaCl). Conditioned medium was harvested after 24 hours as described above. Cell layers were washed twice with ice-cold PBS, and scraped into hot SDS-sample buffer. Medium and cell layer samples were subjected to SDS-PAGE on acrylamide gels, transferred to nitrocellulose membranes and probed with anti-collagen α1(I) C-telopeptide polyclonal antibody LF67 (a generous gift from Larry Fisher), as described.

Figure 8A:
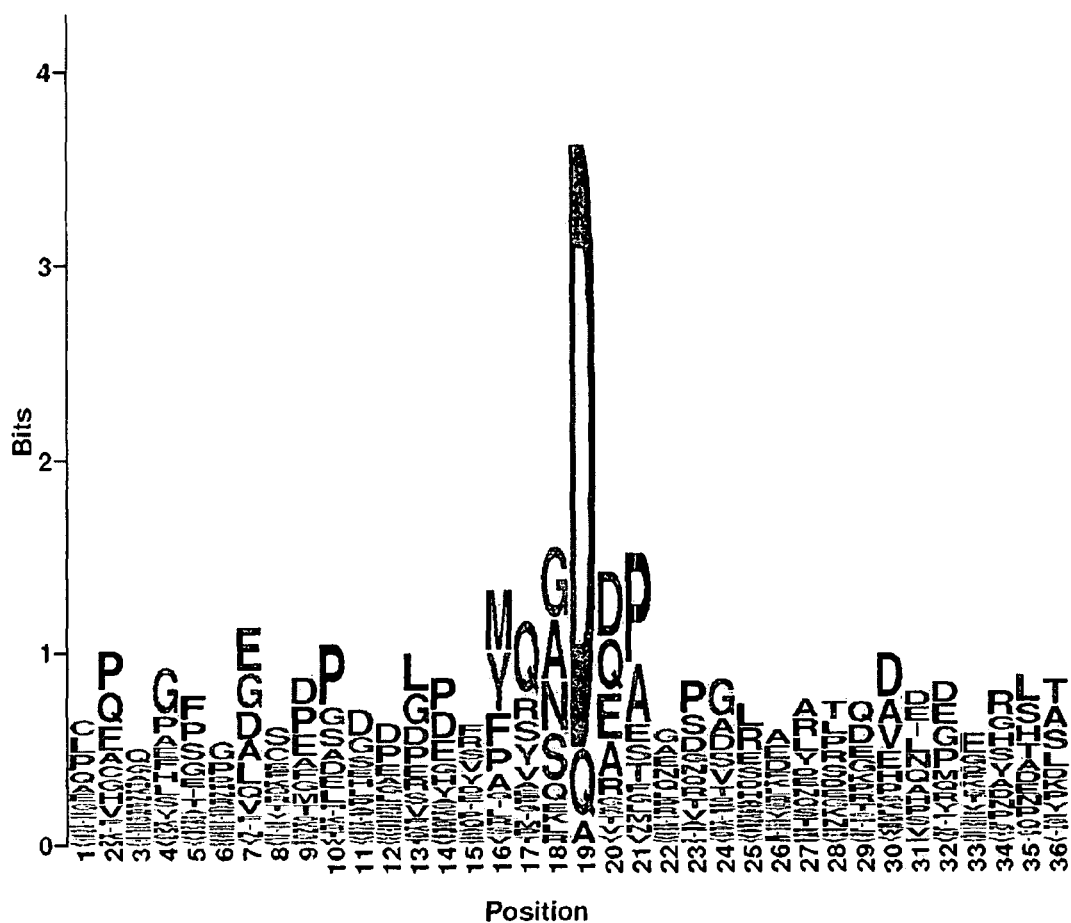
(FIG. 8A) Sequence logo of the thirty-six positions around the cleavage site. The sequence logo was produced by the WebLogo application of Crooks et al. for sequences flanking the BMP-1 cleavage sites of twenty-six published and unpublished substrates. Crooks et al., "WebLogo: a sequence logo generator," Genome Res. 14:1188-1190 (2004). Height of each letter is proportional to the corresponding amino acid and the overall height of each stack is proportional to the sequence conservation at that position. Sequence conservation, measured in bits, has a maximum theoretical value of 4.32. The cleavage site resides between positions eighteen and nineteen.
Figure 8B:
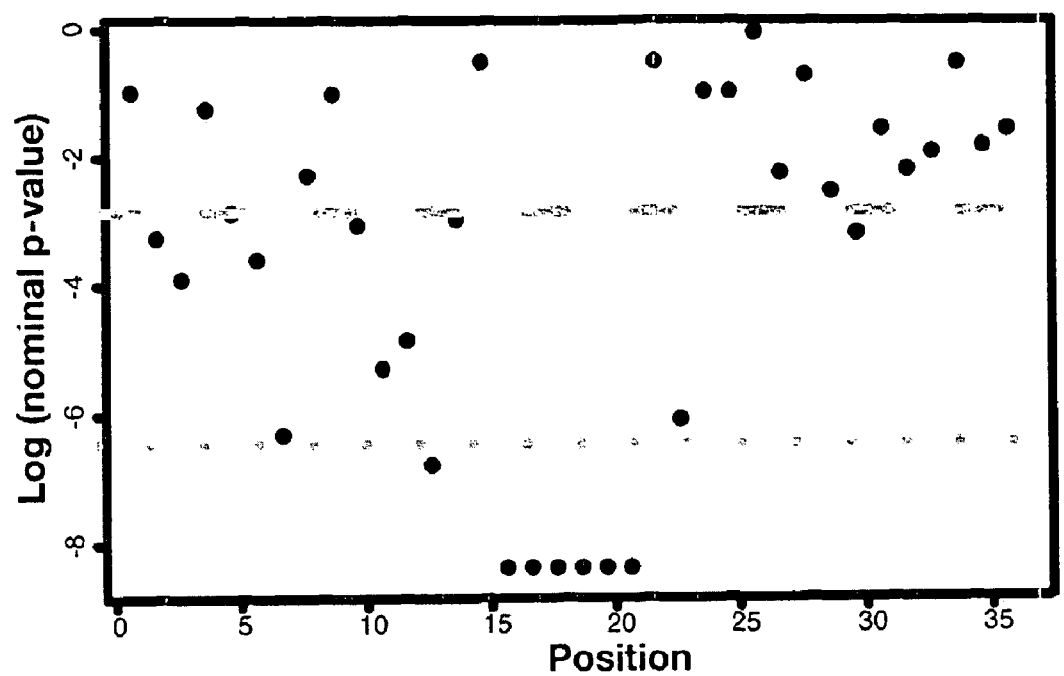
(FIG. 8B) Logged nominal p-values of the goodness of fit tests across the positions around the cleavage site. For each position, a chi-square goodness-of-fit test is employed for testing the null hypothesis that all amino acids have equal probability of occurrence at that site. Plotted are nominal p-values of the tests in the log 10 scale. Horizontal dashed gray lines correspond to p-value cut-offs of 0.05 and 0.05/36, respectively. The second cut-off is the Bonferroni adjusted multiple testing cut-off for controlling the overall Type-I error rate at the nominal level of 0.05.

Amino Acid Specificity Analysis of Identified Cleavage Sites of BMP-1-like Proteinases: We investigated the amino acid sequence specificity of the cleavage sites of twenty-six substrates of BMP-1-like proteinases by considering a thirty-six amino acid region around these sites. The sequence logo of the sequences is given in FIG. 8A, in which the cleavage site is between positions 18 and 19. It is easily observed that positions around the cleavage site exhibit bias towards certain amino acids. We further tested, for each of the thirty-six positions, the null hypothesis that the amino acid composition of the site follows a random amino acid distribution, which assigns an equal occurrence probability to each amino acid. The nominal p-values from the chi-square goodness-of-fit test of each position are plotted in FIG. 8B on the log 10 scale. P-value cut-offs of 0.05 and 0.05/36 are marked as gray dashed horizontal lines on this plot. The second cut-off is the Bonferroni adjusted multiple testing cut-off that provides the control of the overall Type-I error rate at level 0.05. We observe that positions 13, 16, 17, 18, 19, 20 and 21 exhibit strong evidence against the null hypothesis of equal amino acid frequency. Furthermore, although positions 7 and 23 do not pass the Bonferroni adjusted p-value cut-off, they have quite small p-values (0.0016 and 0.002, respectively).

Results:

BMP-1 Cleaves $\alpha_2$M: Perusal of the amino acid sequence of the $\alpha_2$M bait region found a site comprising residues Ser$^{687}$, Asp$^{688}$ and surrounding residues that resembled the majority of known BMP-1 cleavage sites (FIG. 1). The resemblance resided primarily in the placement of Phe$^{684}$ and Tyr$^{686}$ 3 and 4 residues, respectively, NH$_2$-terminal to Asp$^{688}$, since residues with aromatic side chains are frequently found in positions P2-P5, and an Asp is almost always found in the P1' position of previously identified substrates of BMP-1-like proteinases (FIG. 1). Moreover, the majority of previously characterized cleavage sites of BMP-1-like proteinases have residues with small side chains in the P1 positions (FIG. 1), such that the placement of $\alpha_2$M Ser$^{687}$ in relationship to Asp$^{688}$, Phe$^{684}$ and Tyr$^{686}$ is also reminiscent of a BMP-1 cleavage site.

Figure 2A:
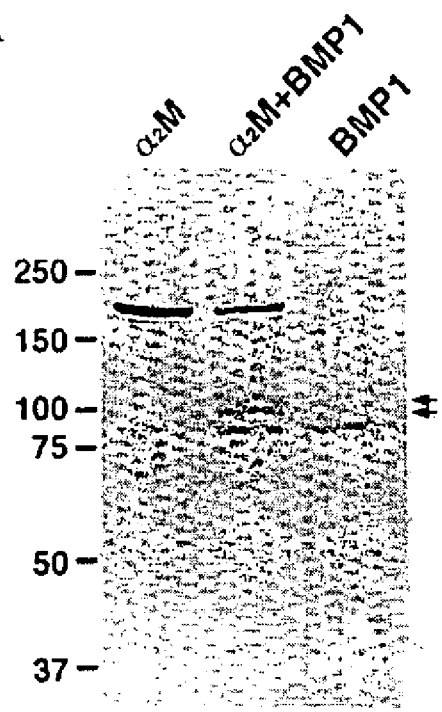
(FIG. 2A) Electrophoretic patterns on an SDS-PAGE gel are compared for human $\alpha_2M$ incubated in the absence ($\alpha_2M$) or presence ($\alpha_2M$+BMP-1) of BMP-1. BMP-1 alone (BMP-1) was electrophoresed in the final lane, to act as a marker for the corresponding band in the $\alpha_2M$+BMP-1 lane. The gel was stained with Coomassie Brilliant Blue R-250. The arrows denote the cleavage products of $\alpha_2M$. Numbers to the left of the gel correspond to the positions and approximate sizes, in kDa, of molecular mass markers.
Figure 2A:
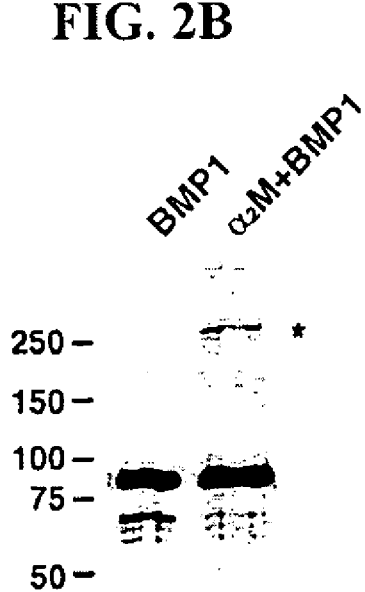
Figure 2A:

As can be seen (FIG. 2A), $\alpha_2$M incubated alone at 37° C. overnight was stable. In contrast, 185-kDa $\alpha_2$M incubated at 37° C. overnight in the presence of BMP-1 was cleaved to produce two bands of ~100- and ~85-kDa. NH$_2$-terminal amino acid sequencing of the 85-kDa band yielded the sequence SVSGKPQYMV (SEQ ID NO:28), which corresponds to the NH$_2$-terminus of secreted $\alpha_2$M. NH$_2$-terminal amino acid sequencing of the 100-kDa band yielded the sequence DVMGRGHXR (SEQ ID NO:29, wherein X represents an unidentified residue), thus demonstrating that BMP-1 cleaves $\alpha_2$M at the predicted site between Ser$^{687}$ and Asp$^{688}$ within the bait region.

Figure 2D:
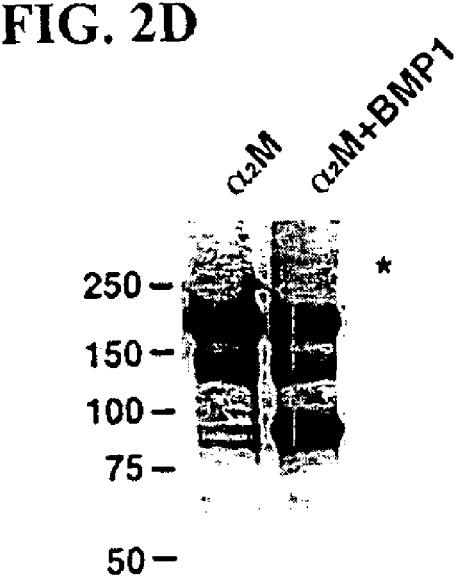
FIG. 2 shows that BMP-1 cleaves and forms a complex with $\alpha_2M$.
(FIGS. 2B and 2C) Western blots, using anti-Flag antibodies for the detection of tagged BMP-1, of $\alpha_2M$ incubated alone ($\alpha_2M$) or with BMP-1 ($\alpha_2M$+BMP-1). BMP-1 starting material [BMP-1(s)] or BMP-1 incubated in the absence of $\alpha_2M$ [BMP-1(0)], were co-electrophoresed as controls. SDS-PAGE of samples was carried out under reducing (FIG. 2B) or non-reducing (FIG. 2C) conditions. Numbers to the left of the blots correspond to the positions and approximate sizes, in kDa, of molecular mass markers. Western blots probed with anti-$\alpha_2M$ antibodies show $\alpha_2M$ to co-localize to the same high molecular weight forms as BMP-1 under both reducing (FIG. 2D) and non-reducing (FIG. 2E) conditions.
Figure 2E:
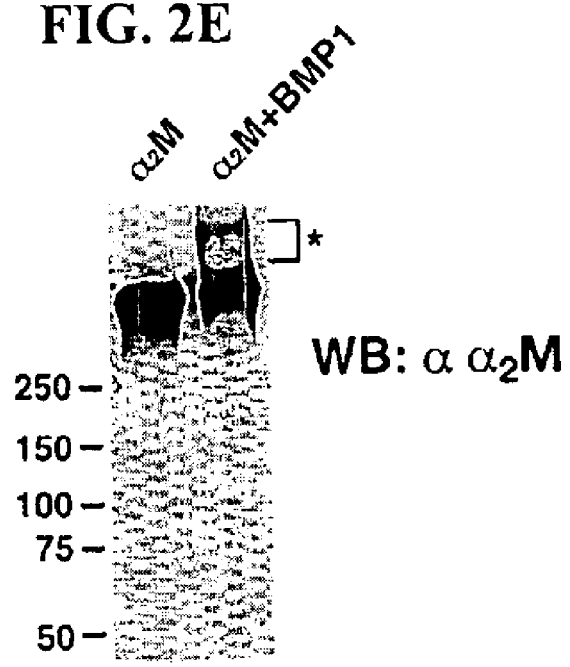

Cleaved $\alpha_2$M Forms a Complex with BMP-1: As can be seen (FIG. 2B), in the presence of $\alpha_2$M, BMP-1, which is normally detected on SDS-PAGE gels as a ~90-kDa monomer can be detected as a ~270-kDa form on a reduced gel. This result is consistent with the interpretation that a single cleaved 100-kDa C-terminal portion of $\alpha_2$M forms a ~190-kDa covalent complex with a single molecule of BMP-1. Under non-reducing conditions (FIG. 2C), BMP-1 can be detected as even higher molecular weight forms. The 85-kDa NH$_2$-terminal and the 100-kDa COOH-terminal fragments of cleaved $\alpha_2$M can remain covalently bound, via disulfide linkage, and this form can be linked to other 85-kDa and 185-kDa forms via disulfide bonds. Thus, the high molecular weight forms observed under non-reducing conditions likely represent BMP-1 covalently bound, via thioester, to 185-, 270- and 375-kDa disulfide bonded oligomers, although the exact identity of each band on the non-reducing-gel remains somewhat speculative. The above interpretations are consistent with Western blots probed with anti-$\alpha_2$M antibodies, which show $\alpha_2$M to co-localize to the same high molecular weight forms as BMP-1 under both reducing (FIG. 2D) and non-reducing (FIG. 2E) conditions. The observation here of covalent binding of BMP-1 to the 100-kDa $\alpha_2$M cleavage product is consistent with the mechanism whereby $\alpha_2$M has been found to covalently bind other proteinases that it inhibits.

Figure 3A:
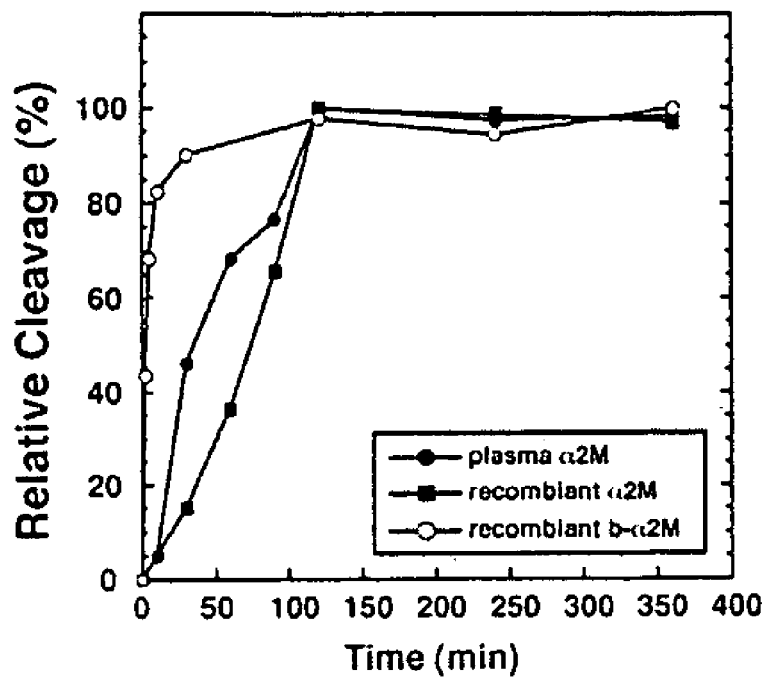
(FIG. 3A) 30 nM BMP-1 was incubated with 30 nM $\alpha_2M$ for 0, 10, 30, 60, 90, 120, 240, and 360 min (plasma $\alpha_2M$ and recombinant wild type $\alpha_2M$) or for 0, 2, 5, 10, 30, 120, 240, and 360 min (b-$\alpha_2M$) at 37° C. Cleavage reaction samples were analyzed by SDS-PAGE on 7.5% acrylamide gels, followed by Western blotting with anti-$\alpha_2M$ antibodies, quantification with NIH Image software, and plotting of relative percentage cleavage of $\alpha_2M$ vs time in minutes.
Figure 3B:
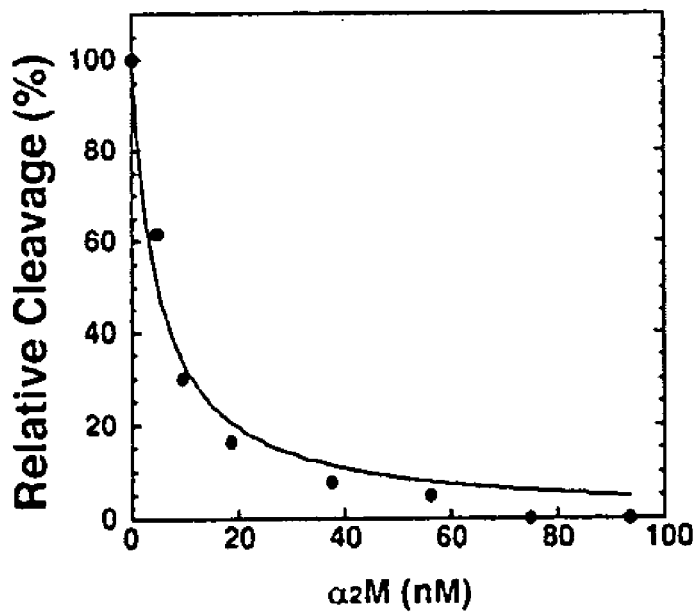
(FIG. 3B) 9.4 nM BMP- was preincubated with 0, 4.7, 9.4, 18.7, 37.5, 56.2, 75.0, or 93.7 nM $\alpha_2M$ for 2 hours at 37° C., followed by incubation with 400 ng $^3$H-radiolabeled type I procollagen. Cleavage reaction samples were analyzed by SDS-PAGE on 5% gels, followed by scanning of autofluorograms, quantification of bands, using NIH Image software, and plotting of relative percent cleavage of procollagen vs nM concentration of $\alpha_2M$. Non-linear regression was performed using SigmaPlot.

$\alpha_2$M Inhibits the pCP Activity of BMP-1: Since the first identified, and best characterized activity of BMP-1 is as a pCP, Kessler E, et al., "Bone morphogenetic protein-1: the type I procollagen C-proteinase," Science 271:360-362 (1996), we next sought to determine whether this activity is inhibited in the presence of $\alpha_2$M. Control experiments demonstrated that BMP-1 achieves maximum cleavage of plasma $\alpha_2$M by 2 hours (FIG. 3A). Thus, to gauge the effect of $\alpha_2$M-BMP-1 interaction on BMP-1 pCP activity, a constant amount of BMP-1 (9.4 nM) was preincubated 2 hours with increasing concentrations of $\alpha_2$M (0, 4.7, 9.4, 18.7, 37.5, 56.2, 75.0, or 93.7 nM), prior to incubation with $^3$H-radiolabeled type I procollagen. Reaction mixtures were subjected to SDS-PAGE and cleavage of procollagen was measured by densitometric analysis of autofluorograms. As can be seen (FIG. 3B), prior incubation with $\alpha_2$M led to potent inhibition of BMP-1 pCP activity, with a calculated IC$_{50}$ of 4.8 nM.

Figure 4:
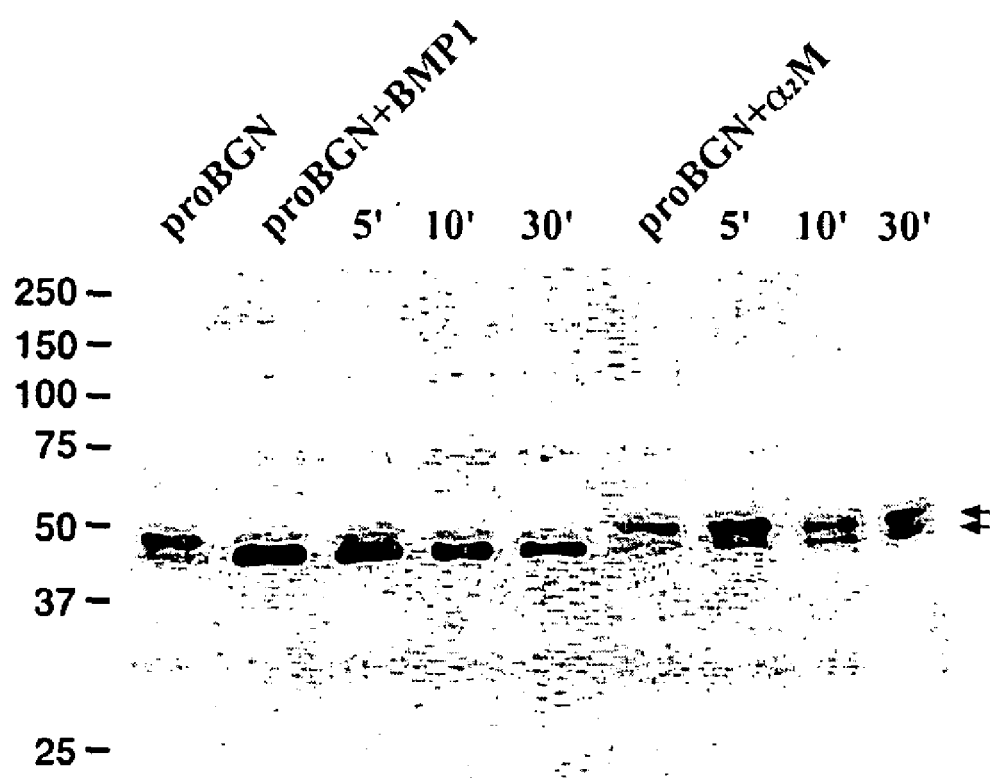
FIG. 4 shows that $\alpha_2M$ inhibits probiglycan cleavage by BMP-1. Western blot analysis, using anti-human biglycan antibody LF-51 (available from National Institutes of Health) raised against amino acids 27-40 of SEQ ID NO:2 (GVLD-PDSVTPTYSA)—the mature region of biglycan—was employed to monitor the processing of probiglycan to biglycan by incubation for 5, 10 or 30 minutes with BMP-1 (proBGN+BMP-1) or with BMP-1 preincubated with $\alpha_2M$ (proBGN+$\alpha_2M$). The upper and lower arrows denote probiglycan and mature biglycan, respectively. Numbers to the left of the blot correspond to the positions and approximate sizes, in kDa, of molecular mass markers.

$\alpha_2$M Inhibits the Cleavage of Probiglycan by BMP-1: As can be seen (FIG. 4), whereas BMP-1 was able to completely convert probiglycan to biglycan after 30 minutes under assay conditions, preincubation with a five-fold molar excess of $\alpha_2$M for 2 hours prior to incubation with probiglycan resulted in inhibition of a majority of probiglycan processing. Thus, $\alpha_2$M appears to be a general inhibitor of BMP-1 activity against various substrates.

Figure 5A:
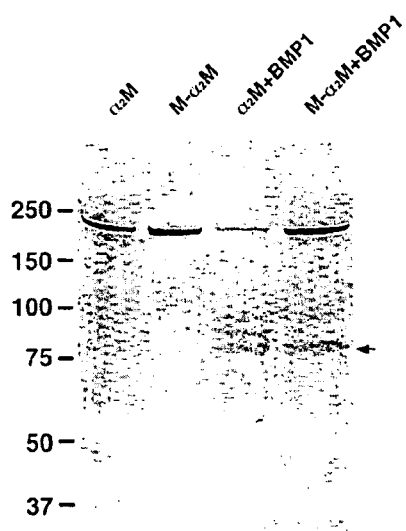
(FIG. 5A) Electrophoretic patterns on an SDS-PAGE gel are compared for human $\alpha_2M$ preincubated either alone ($\alpha_2M$) or with methylamine (M-$\alpha_2M$) and then incubation of BMP-1 with either the untreated ($\alpha_2M$+BMP-1) or methylamine-treated (M-$\alpha_2M$+BMP-1) $\alpha_2M$ samples. The gel was stained with Coomassie Brilliant Blue R-250. The arrow denotes BMP-1. Numbers to the left of the blot and gel correspond to the positions and approximate sizes, in kDa, of molecular mass markers.
Figure 5B:
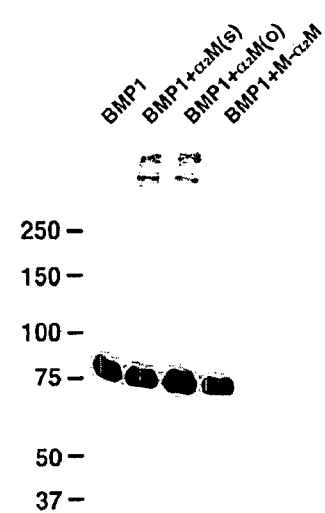
(FIG. 5B) A western blot, using anti-Flag antibodies to detect tagged BMP-1, of BMP-1 alone (BMP-1) or BMP-1 incubated with untreated $\alpha_2M$ [BMP-1+$\alpha_2M$(s)] or with $\alpha_2M$ preincubated in the absence [BMP-1+α$_2$M(o)] or presence [BMP-1+M-α$_2$M] of methylamine.
Figure 5C:
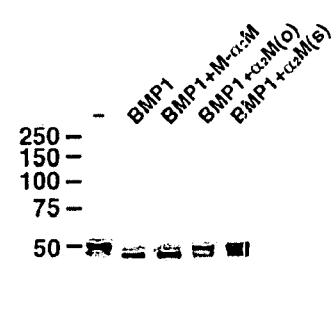
(FIG. 5C) Western blot analysis using LF-51 antibody was employed to monitor the processing of probiglycan to biglycan by incubation alone (−), with BMP-1 (BMP-1), or with BMP-1 preincubated with α$_2$M [BMP-1+α$_2$M(s)] or with BMP-1 preincubated with α$_2$M that had itself been preincubated either in the presence (BMP-1+M-α$_2$M) or absence [BMP-1+α$_2$M(0)] of methylamine. Numbers to the left of the blot correspond to the positions and approximate sizes, in kDa, of molecular mass markers.

Mechanism of $\alpha_2$M Inhibition of BMP-1: As can be seen, BMP-1 was unable to cleave methylamine-treated $\alpha_2$M (FIG. 5A). In addition, $\alpha_2$M pretreated with methylamine did not form complexes with BMP-1 (FIG. 5B). Furthermore, $\alpha_2$M pretreated with methylamine was unable to inhibit the processing of probiglycan to biglycan by BMP-1 (FIG. 5C). Inability of BMP-1 to cleave methylamine-treated $\alpha_2$M was probably the consequence of the conformational change induced in $\alpha_2$M by interaction of methylamine with the $\alpha_2$M thioester. Subsequent to this conformational change, the bait region is presumably not available to proteinases for cleavage. Together, these results bolster the conclusion that inhibition and complexing of BMP-1 by $\alpha_2$M involves formation of a thioester bond between BMP-1 and $\alpha_2$M, and a consequent $\alpha_2$M conformational change.

Example 2

Efficiency of b-$\alpha_2$M

Methods and Results:

b-$\alpha_2$M has enhanced ability to inhibit BMP-1: We previously noted wide differences in the efficiency (e.g., percent cleavage and rate of cleavage) with which different substrates art cleaved by BMP-1 (unpublished data). One of the substrates processed most efficiently by BMP-1 is probiglycan. We therefore sought to determine whether we could enhance the ability of $\alpha_2$M to inhibit BMP-1 by replacing the native bait region with sequences surrounding the probiglycan scissile bond (see FIG. 1).

As can be seen (FIG. 6A), b-$\alpha_2$M is cleaved by BMP-1 more readily than recombinant wild-type $\alpha_2$M (r$\alpha_2$M). When the pCP inhibitory activities of varying concentrations of r$\alpha_2$M and b-$\alpha_2$M were measured (FIGS. 6B and 6C), they led to IC$_{50}$ values of 133 nM and 1.88 nM, respectively. The IC$_{50}$ value of 133 nM for r$\alpha_2$M suggests considerably less effectiveness in BMP-1 inhibition than the 4.82 value obtained for serum $\alpha_2$M (FIG. 3B, Table I); whereas the b-$\alpha_2$M IC$_{50}$ value of 1.88 is consistent with increased inhibitory effectiveness. Although cross-linking experiments demonstrated both recombinant wild type $\alpha_2$M and b-$\alpha_2$M to form tetramers (FIG. 6D), some small difference in folding and/or post-translational modification appears to render the recombinant wild type protein somewhat less effective at BMP-1 inhibition than the corresponding protein from plasma. Importantly however, b-$\alpha_2$M is shown to have markedly improved efficiency in inhibiting BMP-1 compared to wild type $\alpha_2$M prepared under identical conditions, or compared to plasma $\alpha_2$M. The improved efficiency of interaction of b-$\alpha_2$M with BMP-1, compared to wild type $\alpha_2$M, is further illustrated by comparing the rapidity with which b-$\alpha_2$M is cleaved by BMP-1 compared to cleavage of wild type recombinant or plasma $\alpha_2$M (FIG. 3A).

To obtain a quantitative comparison of the rates of interaction of BMP-1 with the various wild type and mutant forms of $\alpha_2$M, we employed the methodology of Enghild et al., supra, which involves quantification of covalent proteinase-$\alpha_2$M complex formation, subsequent to incubation of radiolabeled proteinase with $\alpha_2$M. FIG. 6E shows that subsequent to 2 hour co-incubation of 40 nM $^{35}$S-radiolabeled BMP-1 with 40 nM $\alpha_2$M, considerably more BMP-1 is incorporated into complexes with b-$\alpha_2$M (42% of sample), than with wild type recombinant (12% of sample) or plasma (28% of sample) $\alpha_2$M. Time course experiments conducted with a fixed amount of $^{35}$S-radiolabeled BMP-1 (40 nM) incubated with increasing amounts of each form of $\alpha_2$M, as in Enghild et al., supra, provided K$_i$ values of 25.2, 39.5, and 36.4 nM for b-$\alpha_2$M, and wild type recombinant and plasma $\alpha_2$M, respectively. Second order rate constants obtained from the same data showed b-$\alpha_2$M to be 23.69-fold more effective in interacting with BMP-1 than was recombinant $\alpha_2$M prepared under identical conditions and 15.69-fold more effective than wild type $\alpha_2$M from plasma (Table I).

TABLE I

Relative BMP-1 inhibitory effectiveness of plasma and recombinant $\alpha_2$M forms

| | K$_i$ (nM) | k$_2$ (s$^{-1}$) | 2$^{nd}$-order rate constant (M$^{-1}$s$^{-1}$) | Relative effectiveness |
|---|---|---|---|---|
| Plasma $\alpha_2$M | 25.2 | 0.20 | 8.10 × 10$^6$ | 1.51 |
| Recombinant $\alpha_2$M | 39.5 | 0.21 | 5.36 × 10$^6$ | 1 |
| Recombinant b-$\alpha_2$M | 36.4 | 4.60 | 1.07 × 10$^8$ | 23.69 |

Figure 7A:
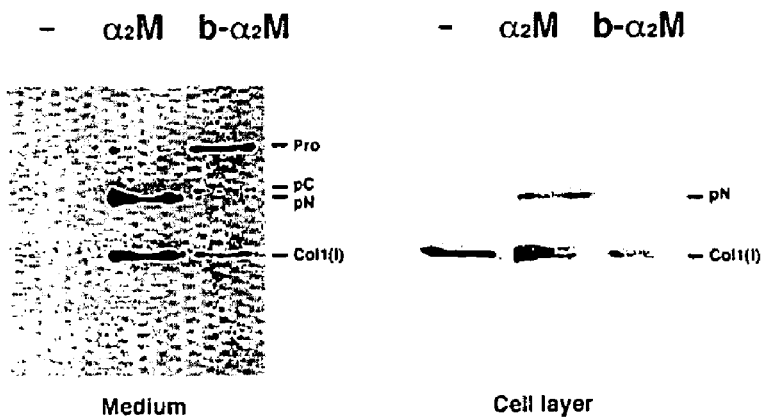
(FIG. 7A) Western blots of media and cell layer samples of MC-3T3 cells incubated in the presence of 20 nM α$_2$M or b-α$_2$M, or an equivalent volume of buffer (−). Blots were probed with anti-α1(I) C-telopeptide antibodies.
Figure 7B:
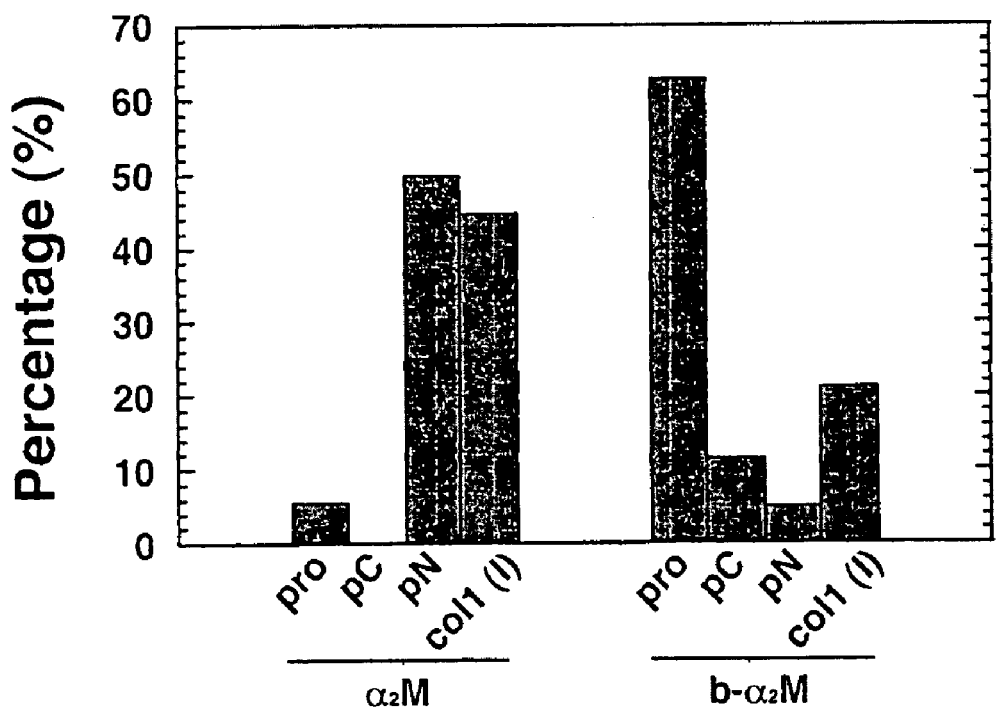
(FIG. 7B) The media sample blot was scanned and quantified using NIH Image software to provide the graft shown in which the percentage of total signal each for the wild-type α$_2$M lane and for the b-α$_2$M lane is given for uncleaved pro-α1(I) chains (pro), pCα1(I) (pC) and pNα1(I) (pN) processing intermediates, and completely processed mature α1(I) chains [col1 (I)]

$\alpha_2$M Inhibition of Procollagen Processing by Cells: As $\alpha_2$M is capable of inhibiting the pCP activity of BMP-1, we determined whether it might be able to inhibit the processing of procollagen by cells. Towards this end, MC-3T3-E1 murine osteoblastic cells were incubated either alone or in the presence of r$\alpha_2$M or b-$\alpha_2$M. The levels of processing of procollagen and insertion into the cell layer were compared. As can be seen (FIG. 7), MC-3T3 processing of procollagen was inhibited by both recombinant wild type (r) $\alpha_2$M and mutant (b)-$\alpha_2$M. However, in the case of media from r$\alpha_2$M-treated cells, most detectable collagenous material was the in the form of processing intermediate pN$\alpha$1(I) (in which the N-, but not the C-propeptide is retained), or mature α1(I) chains; whereas, in media from b-α$_2$M-treated cells, most detectable collagenous material was in the form of unprocessed pro-α1(I) chains (FIGS. 7A and 7B). These results show efficient inhibition of cellular BMP-1-like proteins by b-α$_2$M, and less efficient inhibition by wild-type α$_2$M.

The appearances of pNα1(I) chains in the wild type α$_2$M-treated sample and of procollagen in the b-α$_2$M-treated sample indicate that both forms of α$_2$M are able to inhibit N-propeptide cleavage in cell culture by the proteinase ADAMTS-2. This is consistent with a previous report that α$_2$M is capable of inhibiting ADAMTS-2 in vitro. Colige A, et al., "Domains and maturation processes that regulate the activity of ADAMTS-2, a metalloproteinase cleaving the aminopropeptide of fibrillar procollagens types I-III and V," J. Biol. Chem. 280:34397-34408 (2005). b-α$_2$M may retain the ability to inhibit ADAMTS-2, as a potential ADAMTS-2 cleavage site at the N-terminus of the native bait region is retained in the b-α$_2$M sequence (FIG. 1).

Collagen was not detected in the media of untreated cells (FIG. 7A), presumably because of efficient processing and insertion of mature collagen into the cell layer. Untreated cell layers contained only fully processed mature α1(I) chains, whereas cell layers of cultures treated with either wild type α$_2$M or b-α$_2$M contained both mature α1(I) chains and pNα1 (I) forms (FIG. 7A). pCα1(I) forms (in which the C-, but not the N-propeptide is retained) were detected only in the media of b-α$_2$M-treated cultures (FIG. 7A), and were not found in the cell layers of any of the cultures, presumably because pCα1(I) chains are not inserted into ECM under normal circumstances. Treatment of MC-3T3-E1 cells with plasma α$_2$M (data not shown), yielded effects on procollagen processing similar to those obtained from treatment of cells with recombinant wild type α$_2$M.

Example 3

Prophetic

Treatment of Fibrotic Disorders

A subject experiencing or at risk for a fibrotic disorder, such as lung fibrosis, kidney fibrosis or keloids is administered a an inhalant, injection or topical lotion (e.g., cream or ointment), respectively, comprising α$_2$M or a modified α$_2$M in an amount effective to reduce occurrence or severity of the fibrotic disorder. For example, a subject predisposed to keloids applies a topical cream, lotion or ointment comprising α$_2$M or a modified α$_2$M at least once a day. After treatment, fibrosis is prevented or reduced.

The invention can be tested by ascertaining anti-fibrotic effects in a model system in which pulmonary fibrosis is induced in mice via intratracheal (IT) instillation of bleomycin (2 U/kg). At 3 and 5 days following instillation with bleomycin, mice can be given IT installations of 40 nM wild type or altered α$_2$M (30 μl/mouse), or PBS, as a negative control. Two weeks after initial bleomycin instillation, lung tissue can be isolated and subjected to histological (via hematoxylin and eosin staining and light microscopy) and ultrastructural (electron microscopic) analyses to test for septal thickening and reduction of alveolar space, typical of pulmonary fibrosis. Similarly, Masson trichrome-staining of paraffin sections and a Sircol assay, can be performed to determine the extent of deposition of collagenous matrix in lung (a strong indicator of fibrosis). These and additional tests of fibrotic outcome can be performed essentially as described previously. See, e.g., Giri S, et al., "Antifibrotic effect of Decorin in a bleomycin hamster model of lung fibrosis," Biochem. Pharmacol. 54:1205-1216 (1997); and Avivi-Green C, et al., "Discoidin domain receptor 1-deficient mice are resistant to bleomycin-induced lung fibrosis," Am. J. Respir. Crit. Care Med. 174:420-427 (2006), each of which is incorporated herein by reference as if set forth in its entirety.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. An engineered $\alpha_2$-macroglobulin protein comprising an engineered bait region, the engineered bait region being a bone morphogenetic protein-1 bait region from a protein other than $\alpha_2$-macroglobulin that is cleaved by BMP-1, wherein the engineered $\alpha_2$-macroglobulin protein is characterized by an at least about 25-fold enhanced BMP-1 inhibitory effectiveness compared to a wild type $\alpha_2$-macroglobulin protein, and wherein the protein other than $\alpha$2-macroglobulin is probiglycan.

2. The protein of claim 1, wherein the protein other than $\alpha_2$-macroglobulin is probiglycan from a human.

3. The protein of claim 1, wherein the bait region of the protein other than $\alpha_2$-macroglobulin consists of an amino acid sequence encoded by a nucleic acid sequence amplifiable from genomic DNA from a human using SEQ ID NO:26 and SEQ ID NO:27 as amplification primers.

4. The protein of claim 1, wherein the engineered bait region comprises the amino acid sequence of SEQ ID NO: 2.

5. A method of inhibiting a bone morphogenetic protein-1 (BMP-1)-like proteinase in a human or non-human animal experiencing or susceptible to a fibrotic disorder caused by the BMP-1-like proteinase, the method comprising the step of: administering to the animal an amount of an inhibitor of the BMP-1-like proteinase effective to reduce BMP-1-like proteinase activity in the animal, where the reduction is characterized by a reduction in severity or occurrence of the fibrotic disorder, and wherein the inhibitor of the BMP-1-like proteinase is an engineered $\alpha_2$-macroglobulin protein according to claim 1.

6. The method of claim 5, wherein the bait region of the protein other than $\alpha_2$-macroglobulin consists of an amino acid sequence encoded by a nucleic acid sequence amplifiable from genomic DNA from a human using SEQ ID NO:26 and SEQ ID NO:27 as amplification primers.

7. The method of claim 5, wherein the bait region comprises the amino acid sequence of SEQ ID NO:2.

8. The method of claim 5, wherein the bone morphogenetic protein-1-like proteinase is selected from the group consisting of bone morphogenetic protein-1, mammalian Tolloid, mammalian Tolloid-like 1 and mammalian Tolloid-like 2.

9. The method of claim 5, wherein the fibrotic disorder is selected from the group consisting of a keloid or other abnormal wound healing, a surgical adhesion and a deep-seated fibrosis of an organ.

* * * * *

SEQUENCE LISTING

<160> NUMBER OF SEQ ID NOS: 29

<210> SEQ ID NO 1
<211> LENGTH: 39
<212> TYPE: PRT
<213> ORGANISM: Homo sapiens

<400> SEQUENCE: 1

Pro Gln Leu Gln Gln Tyr Glu Met His Gly Pro Glu Gly Leu Arg Val
1               5                   10                  15

Gly Phe Tyr Glu Ser Asp Val Met Gly Arg Gly His Ala Arg Leu Val
            20                  25                  30

His Val Glu Glu Pro His Thr
        35

<210> SEQ ID NO 2
<211> LENGTH: 42

-continued

```
<212> TYPE: PRT
<213> ORGANISM: Artificial
<220> FEATURE:
<223> OTHER INFORMATION: Synthetic polynucleotide

<400> SEQUENCE: 2

Pro Gln Phe Trp Asp Phe Thr Leu Asp Asp Gly Pro Phe Met Met Asn
1               5                   10                  15

Asp Glu Glu Ala Ser Gly Ala Asp Thr Ser Gly Val Leu Asp Pro Asp
                20                  25                  30

Ser Val Thr Pro Thr Tyr Ser Ala Met Val
            35                  40

<210> SEQ ID NO 3
<211> LENGTH: 16
<212> TYPE: PRT
<213> ORGANISM: Mus musculus

<400> SEQUENCE: 3

Leu Asp Leu His Asp Phe Gln Gly Asp Ala Leu Gln Pro Glu Asp Phe
1               5                   10                  15

<210> SEQ ID NO 4
<211> LENGTH: 16
<212> TYPE: PRT
<213> ORGANISM: Mus musculus

<400> SEQUENCE: 4

Ile Asp Gln Tyr Asp Val Gln Arg Asp Asp Ser Ser Asp Gly Ser Leu
1               5                   10                  15

<210> SEQ ID NO 5
<211> LENGTH: 16
<212> TYPE: PRT
<213> ORGANISM: Homo sapiens

<400> SEQUENCE: 5

Asp Gly Gly Arg Tyr Tyr Arg Ala Asp Asp Ala Asn Val Val Arg Asp
1               5                   10                  15

<210> SEQ ID NO 6
<211> LENGTH: 16
<212> TYPE: PRT
<213> ORGANISM: Homo sapiens

<400> SEQUENCE: 6

Tyr Asp Gly Asp Phe Tyr Arg Ala Asp Gln Pro Arg Ser Ala Pro Ser
1               5                   10                  15

<210> SEQ ID NO 7
<211> LENGTH: 16
<212> TYPE: PRT
<213> ORGANISM: Homo sapiens

<400> SEQUENCE: 7

Asp Pro Leu Gln Tyr Met Arg Ala Asp Gln Ala Ala Gly Gly Leu Arg
1               5                   10                  15

<210> SEQ ID NO 8
<211> LENGTH: 16
<212> TYPE: PRT
<213> ORGANISM: Homo sapiens

<400> SEQUENCE: 8
```

-continued

```
Gly Gly Phe Ala Pro Tyr Tyr Gly Asp Glu Pro Met Asp Phe Lys Ile
1               5                   10                  15

<210> SEQ ID NO 9
<211> LENGTH: 16
<212> TYPE: PRT
<213> ORGANISM: Homo sapiens

<400> SEQUENCE: 9

Asp Pro Leu Pro Glu Phe Thr Glu Asp Gln Ala Ala Pro Asp Asp Lys
1               5                   10                  15

<210> SEQ ID NO 10
<211> LENGTH: 16
<212> TYPE: PRT
<213> ORGANISM: Homo sapiens

<400> SEQUENCE: 10

Arg Pro Leu Pro Ser Tyr Ala Ala Asp Thr Ala Gly Ser Gln Leu His
1               5                   10                  15

<210> SEQ ID NO 11
<211> LENGTH: 16
<212> TYPE: PRT
<213> ORGANISM: Homo sapiens

<400> SEQUENCE: 11

Asp Thr Gly Asp Cys Tyr Ser Gly Asp Glu Asn Pro Asp Ile Glu Cys
1               5                   10                  15

<210> SEQ ID NO 12
<211> LENGTH: 16
<212> TYPE: PRT
<213> ORGANISM: Homo sapiens

<400> SEQUENCE: 12

Asp Asp Gly Pro Phe Met Met Asn Asp Glu Glu Ala Ser Gly Ala Asp
1               5                   10                  15

<210> SEQ ID NO 13
<211> LENGTH: 16
<212> TYPE: PRT
<213> ORGANISM: Mus musculus

<400> SEQUENCE: 13

Asp Pro Glu His Arg Ser Tyr Ser Asp Arg Gly Glu Pro Gly Val Gly
1               5                   10                  15

<210> SEQ ID NO 14
<211> LENGTH: 4678
<212> TYPE: DNA
<213> ORGANISM: Homo sapiens
<220> FEATURE:
<221> NAME/KEY: CDS
<222> LOCATION: (114)..(4535)

<400> SEQUENCE: 14
gcacacagag cagcataaag cccagttgct ttgggaagtg tttgggacca gatggattgt      60
agggagtagg gtacaataca gtctgttctc ctccagctcc ttctttctgc aac atg       116
                                                              Met
                                                                1 ggg aag aac aaa ctc ctt cat cca agt ctg gtt ctt ctc ctc ttg gtc      164
Gly Lys Asn Lys Leu Leu His Pro Ser Leu Val Leu Leu Leu Leu Val
        5                   10                  15
```

```
ctc ctg ccc aca gac gcc tca gtc tct gga aaa ccg cag tat atg gtt     212
Leu Leu Pro Thr Asp Ala Ser Val Ser Gly Lys Pro Gln Tyr Met Val
         20              25              30 ctg gtc ccc tcc ctg ctc cac act gag acc act gag aag ggc tgt gtc     260
Leu Val Pro Ser Leu Leu His Thr Glu Thr Thr Glu Lys Gly Cys Val
 35              40              45 ctt ctg agc tac ctg aat gag aca gtg act gta agt gct tcc ttg gag     308
Leu Leu Ser Tyr Leu Asn Glu Thr Val Thr Val Ser Ala Ser Leu Glu
 50              55              60              65 tct gtc agg gga aac agg agc ctc ttc act gac ctg gag gcg gag aat     356
Ser Val Arg Gly Asn Arg Ser Leu Phe Thr Asp Leu Glu Ala Glu Asn
             70              75              80 gac gta ctc cac tgt gtc gcc ttc gct gtc cca aag tct tca tcc aat     404
Asp Val Leu His Cys Val Ala Phe Ala Val Pro Lys Ser Ser Ser Asn
                 85              90              95 gag gag gta atg ttc ctc act gtc caa gtg aaa gga cca acc caa gaa     452
Glu Glu Val Met Phe Leu Thr Val Gln Val Lys Gly Pro Thr Gln Glu
                 100             105             110 ttt aag aag cgg acc aca gtg atg gtt aag aac gag gac agt ctg gtc     500
Phe Lys Lys Arg Thr Thr Val Met Val Lys Asn Glu Asp Ser Leu Val
 115             120             125 ttt gtc cag aca gac aaa tca atc tac aaa cca ggg cag aca gtg aaa     548
Phe Val Gln Thr Asp Lys Ser Ile Tyr Lys Pro Gly Gln Thr Val Lys
130             135             140             145 ttt cgt gtt gtc tcc atg gat gaa aac ttt cac ccc ctg aat gag ttg     596
Phe Arg Val Val Ser Met Asp Glu Asn Phe His Pro Leu Asn Glu Leu
                 150             155             160 att cca cta gta tac att cag gat ccc aaa gga aat cgc atc gca caa     644
Ile Pro Leu Val Tyr Ile Gln Asp Pro Lys Gly Asn Arg Ile Ala Gln
                 165             170             175 tgg cag agt ttc cag tta gag ggt ggc ctc aag caa ttt tct ttt ccc     692
Trp Gln Ser Phe Gln Leu Glu Gly Gly Leu Lys Gln Phe Ser Phe Pro
             180             185             190 ctc tca tca gag ccc ttc cag ggc tcc tac aag gtg gtg gta cag aag     740
Leu Ser Ser Glu Pro Phe Gln Gly Ser Tyr Lys Val Val Val Gln Lys
 195             200             205 aaa tca ggt gga agg aca gag cac cct ttc acc gtg gag gaa ttt gtt     788
Lys Ser Gly Gly Arg Thr Glu His Pro Phe Thr Val Glu Glu Phe Val
210             215             220             225 ctt ccc aag ttt gaa gta caa gta aca gtg cca aag ata atc acc atc     836
Leu Pro Lys Phe Glu Val Gln Val Thr Val Pro Lys Ile Ile Thr Ile
                 230             235             240 ttg gaa gaa gag atg aat gta tca gtg tgt ggc cta tac aca tat ggg     884
Leu Glu Glu Glu Met Asn Val Ser Val Cys Gly Leu Tyr Thr Tyr Gly
             245             250             255 aag cct gtc cct gga cat gtg act gtg agc att tgc aga aag tat agt     932
Lys Pro Val Pro Gly His Val Thr Val Ser Ile Cys Arg Lys Tyr Ser
         260             265             270 gac gct tcc gac tgc cac ggt gaa gat tca cag gct ttc tgt gag aaa     980
Asp Ala Ser Asp Cys His Gly Glu Asp Ser Gln Ala Phe Cys Glu Lys
 275             280             285 ttc agt gga cag cta aac agc cat ggc tgc ttc tat cag caa gta aaa    1028
Phe Ser Gly Gln Leu Asn Ser His Gly Cys Phe Tyr Gln Gln Val Lys
290             295             300             305 acc aag gtc ttc cag ctg aag agg aag gag tat gaa atg aaa ctt cac    1076
Thr Lys Val Phe Gln Leu Lys Arg Lys Glu Tyr Glu Met Lys Leu His
                 310             315             320 act gag gcc cag atc caa gaa gaa gga aca gtg gtg gaa ttg act gga    1124
Thr Glu Ala Gln Ile Gln Glu Glu Gly Thr Val Val Glu Leu Thr Gly
             325             330             335
```

```
agg cag tcc agt gaa atc aca aga acc ata acc aaa ctc tca ttt gtg      1172
Arg Gln Ser Ser Glu Ile Thr Arg Thr Ile Thr Lys Leu Ser Phe Val
        340                 345                 350 aaa gtg gac tca cac ttt cga cag gga att ccc ttc ttt ggg cag gtg      1220
Lys Val Asp Ser His Phe Arg Gln Gly Ile Pro Phe Phe Gly Gln Val
    355                 360                 365 cgc cta gta gat ggg aaa ggc gtc cct ata cca aat aaa gtc ata ttc      1268
Arg Leu Val Asp Gly Lys Gly Val Pro Ile Pro Asn Lys Val Ile Phe
370                 375                 380                 385 atc aga gga aat gaa gca aac tat tac tcc aat gct acc acg gat gag      1316
Ile Arg Gly Asn Glu Ala Asn Tyr Tyr Ser Asn Ala Thr Thr Asp Glu
                390                 395                 400 cat ggc ctt gta cag ttc tct atc aac acc acc aat gtt atg ggt acc      1364
His Gly Leu Val Gln Phe Ser Ile Asn Thr Thr Asn Val Met Gly Thr
            405                 410                 415 tct ctt act gtt agg gtc aat tac aag gat cgt agt ccc tgt tac ggc      1412
Ser Leu Thr Val Arg Val Asn Tyr Lys Asp Arg Ser Pro Cys Tyr Gly
        420                 425                 430 tac cag tgg gtg tca gaa gaa cac gaa gag gca cat cac act gct tat      1460
Tyr Gln Trp Val Ser Glu Glu His Glu Glu Ala His His Thr Ala Tyr
    435                 440                 445 ctt gtg ttc tcc cca agc aag agc ttt gtc cac ctt gag ccc atg tct      1508
Leu Val Phe Ser Pro Ser Lys Ser Phe Val His Leu Glu Pro Met Ser
450                 455                 460                 465 cat gaa cta ccc tgt ggc cat act cag aca gtc cag gca cat tat att      1556
His Glu Leu Pro Cys Gly His Thr Gln Thr Val Gln Ala His Tyr Ile
                470                 475                 480 ctg aat gga ggc acc ctg ctg ggg ctg aag aag ctc tcc ttc tat tat      1604
Leu Asn Gly Gly Thr Leu Leu Gly Leu Lys Lys Leu Ser Phe Tyr Tyr
            485                 490                 495 ctg ata atg gca aag gga ggc att gtc cga act ggg act cat gga ctg      1652
Leu Ile Met Ala Lys Gly Gly Ile Val Arg Thr Gly Thr His Gly Leu
        500                 505                 510 ctt gtg aag cag gaa gac atg aag ggc cat ttt tcc atc tca atc cct      1700
Leu Val Lys Gln Glu Asp Met Lys Gly His Phe Ser Ile Ser Ile Pro
    515                 520                 525 gtg aag tca gac att gct cct gtc gct cgg ttg ctc atc tat gct gtt      1748
Val Lys Ser Asp Ile Ala Pro Val Ala Arg Leu Leu Ile Tyr Ala Val
530                 535                 540                 545 tta cct acc ggg gac gtg att ggg gat tct gca aaa tat gat gtt gaa      1796
Leu Pro Thr Gly Asp Val Ile Gly Asp Ser Ala Lys Tyr Asp Val Glu
                550                 555                 560 aat tgt ctg gcc aac aag gtg gat ttg agc ttc agc cca tca caa agt      1844
Asn Cys Leu Ala Asn Lys Val Asp Leu Ser Phe Ser Pro Ser Gln Ser
            565                 570                 575 ctc cca gcc tca cac gcc cac ctg cga gtc aca gcg gct cct cag tcc      1892
Leu Pro Ala Ser His Ala His Leu Arg Val Thr Ala Ala Pro Gln Ser
        580                 585                 590 gtc tgc gcc ctc cgt gct gtg gac caa agc gtg ctc ctc atg aag cct      1940
Val Cys Ala Leu Arg Ala Val Asp Gln Ser Val Leu Leu Met Lys Pro
    595                 600                 605 gat gct gag ctc tcg gcg tcc tcg gtt tac aac ctg cta cca gaa aag      1988
Asp Ala Glu Leu Ser Ala Ser Ser Val Tyr Asn Leu Leu Pro Glu Lys
610                 615                 620                 625 gac ctc act ggc ttc cct ggg cct ttg aat gac cag gac gat gaa gac      2036
Asp Leu Thr Gly Phe Pro Gly Pro Leu Asn Asp Gln Asp Asp Glu Asp
                630                 635                 640 tgc atc aat cgt cat aat gtc tat att aat gga atc aca tat act cca      2084
Cys Ile Asn Arg His Asn Val Tyr Ile Asn Gly Ile Thr Tyr Thr Pro
```

-continued

| | | | |
|---|---|---|---|
| | 645 | 650 | 655 |

| | | |
|---|---|---|
| gta tca agt aca aat gaa aag gat atg tac agc ttc cta gag gac atg<br>Val Ser Ser Thr Asn Glu Lys Asp Met Tyr Ser Phe Leu Glu Asp Met<br>    660                        665                        670 | 2132 |
| ggc tta aag gca ttc acc aac tca aag att cgt aaa ccc aaa atg tgt<br>Gly Leu Lys Ala Phe Thr Asn Ser Lys Ile Arg Lys Pro Lys Met Cys<br>675                        680                        685 | 2180 |
| cca cag ctt caa cag tat gaa atg cat gga cct gaa ggt cta cgt gta<br>Pro Gln Leu Gln Gln Tyr Glu Met His Gly Pro Glu Gly Leu Arg Val<br>690                        695                        700                        705 | 2228 |
| ggt ttt tat gag tca gat gta atg gga aga ggc cat gca cgc ctg gtg<br>Gly Phe Tyr Glu Ser Asp Val Met Gly Arg Gly His Ala Arg Leu Val<br>                        710                        715                        720 | 2276 |
| cat gtt gaa gag cct cac acg gag acc gta cga aag tac ttc cct gag<br>His Val Glu Glu Pro His Thr Glu Thr Val Arg Lys Tyr Phe Pro Glu<br>                        725                        730                        735 | 2324 |
| aca tgg atc tgg gat ttg gtg gtg gta aac tca gca ggt gtg gct gag<br>Thr Trp Ile Trp Asp Leu Val Val Val Asn Ser Ala Gly Val Ala Glu<br>                        740                        745                        750 | 2372 |
| gta gga gta aca gtc cct gac acc atc acc gag tgg aag gca ggg gcc<br>Val Gly Val Thr Val Pro Asp Thr Ile Thr Glu Trp Lys Ala Gly Ala<br>755                        760                        765 | 2420 |
| ttc tgc ctg tct gaa gat gct gga ctt ggt atc tct tcc act gcc tct<br>Phe Cys Leu Ser Glu Asp Ala Gly Leu Gly Ile Ser Ser Thr Ala Ser<br>770                        775                        780                        785 | 2468 |
| ctc cga gcc ttc cag ccc ttc ttt gtg gag ctc aca atg cct tac tct<br>Leu Arg Ala Phe Gln Pro Phe Phe Val Glu Leu Thr Met Pro Tyr Ser<br>                        790                        795                        800 | 2516 |
| gtg att cgt gga gag gcc ttc aca ctc aag gcc acg tcc cta aac tac<br>Val Ile Arg Gly Glu Ala Phe Thr Leu Lys Ala Thr Val Leu Asn Tyr<br>                        805                        810                        815 | 2564 |
| ctt ccc aaa tgc atc cgg gtc agt gtg cag ctg gaa gcc tct ccc gcc<br>Leu Pro Lys Cys Ile Arg Val Ser Val Gln Leu Glu Ala Ser Pro Ala<br>820                        825                        830 | 2612 |
| ttc cta gct gtc cca gtg gag aag gaa caa gcg cct cac tgc atc tgt<br>Phe Leu Ala Val Pro Val Glu Lys Glu Gln Ala Pro His Cys Ile Cys<br>835                        840                        845 | 2660 |
| gca aac ggg cgg caa act gtg tcc tgg gca gta acc cca aag tca tta<br>Ala Asn Gly Arg Gln Thr Val Ser Trp Ala Val Thr Pro Lys Ser Leu<br>850                        855                        860                        865 | 2708 |
| gga aat gtg aat ttc act gtg agc gca gag gca cta gag tct caa gag<br>Gly Asn Val Asn Phe Thr Val Ser Ala Glu Ala Leu Glu Ser Gln Glu<br>                        870                        875                        880 | 2756 |
| ctg tgt ggg act gag gtg cct tca gtt cct gaa cac gga agg aaa gac<br>Leu Cys Gly Thr Glu Val Pro Ser Val Pro Glu His Gly Arg Lys Asp<br>                        885                        890                        895 | 2804 |
| aca gtc atc aag cct ctg ttg gtt gaa cct gaa gga cta gag aag gaa<br>Thr Val Ile Lys Pro Leu Leu Val Glu Pro Glu Gly Leu Glu Lys Glu<br>900                        905                        910 | 2852 |
| aca aca ttc aac tcc cta ctt tgt cca tca ggt ggt gag gtt tct gaa<br>Thr Thr Phe Asn Ser Leu Leu Cys Pro Ser Gly Gly Glu Val Ser Glu<br>915                        920                        925 | 2900 |
| gaa tta tcc ctg aaa ctg cca cca aat gtg gta gaa gaa tct gcc cga<br>Glu Leu Ser Leu Lys Leu Pro Pro Asn Val Val Glu Glu Ser Ala Arg<br>930                        935                        940                        945 | 2948 |
| gct tct gtc tca gtt ttg gga gac ata tta ggc tct gcc atg caa aac<br>Ala Ser Val Ser Val Leu Gly Asp Ile Leu Gly Ser Ala Met Gln Asn<br>                        950                        955                        960 | 2996 |
| aca caa aat ctt ctc cag atg ccc tat ggc tgt gga gag cag aat atg | 3044 |

-continued

```
Thr Gln Asn Leu Leu Gln Met Pro Tyr Gly Cys Gly Glu Gln Asn Met
            965                 970                 975 gtc ctc ttt gct cct aac atc tat gta ctg gat tat cta aat gaa aca    3092
Val Leu Phe Ala Pro Asn Ile Tyr Val Leu Asp Tyr Leu Asn Glu Thr
            980                 985                 990 cag cag ctt act cca gag atc aag tcc aag gcc att ggc tat ctc aac    3140
Gln Gln Leu Thr Pro Glu Ile Lys Ser Lys Ala Ile Gly Tyr Leu Asn
        995                 1000                1005 act ggt tac cag aga cag ttg aac tac aaa cac tat gat ggc tcc        3185
Thr Gly Tyr Gln Arg Gln Leu Asn Tyr Lys His Tyr Asp Gly Ser
1010                1015                1020 tac agc acc ttt ggg gag cga tat ggc agg aac cag ggc aac acc        3230
Tyr Ser Thr Phe Gly Glu Arg Tyr Gly Arg Asn Gln Gly Asn Thr
1025                1030                1035 tgg ctc aca gcc ttt gtt ctg aag act ttt gcc caa gct cga gcc        3275
Trp Leu Thr Ala Phe Val Leu Lys Thr Phe Ala Gln Ala Arg Ala
1040                1045                1050 tac atc ttc atc gat gaa gca cac att acc caa gcc ctc ata tgg        3320
Tyr Ile Phe Ile Asp Glu Ala His Ile Thr Gln Ala Leu Ile Trp
1055                1060                1065 ctc tcc cag agg cag aag gac aat ggc tgt ttc agg agc tct ggg        3365
Leu Ser Gln Arg Gln Lys Asp Asn Gly Cys Phe Arg Ser Ser Gly
1070                1075                1080 tca ctg ctc aac aat gcc ata aag gga gga gta gaa gat gaa gtg        3410
Ser Leu Leu Asn Asn Ala Ile Lys Gly Gly Val Glu Asp Glu Val
1085                1090                1095 acc ctc tcc gcc tat atc acc atc gcc ctt ctg gag att cct ctc        3455
Thr Leu Ser Ala Tyr Ile Thr Ile Ala Leu Leu Glu Ile Pro Leu
1100                1105                1110 aca gtc act cac cct gtt gtc cgc aat gcc ctg ttt tgc ctg gag        3500
Thr Val Thr His Pro Val Val Arg Asn Ala Leu Phe Cys Leu Glu
1115                1120                1125 tca gcc tgg aag aca gca caa gaa ggg gac cat ggc agc cat gta        3545
Ser Ala Trp Lys Thr Ala Gln Glu Gly Asp His Gly Ser His Val
1130                1135                1140 tat acc aaa gca ctg ctg gcc tat gct ttt gcc ctg gca ggt aac        3590
Tyr Thr Lys Ala Leu Leu Ala Tyr Ala Phe Ala Leu Ala Gly Asn
1145                1150                1155 cag gac aag agg aag gaa gta ctc aag tca ctt aat gag gaa gct        3635
Gln Asp Lys Arg Lys Glu Val Leu Lys Ser Leu Asn Glu Glu Ala
1160                1165                1170 gtg aag aaa gac aac tct gtc cat tgg gag cgc cct cag aaa ccc        3680
Val Lys Lys Asp Asn Ser Val His Trp Glu Arg Pro Gln Lys Pro
1175                1180                1185 aag gca cca gtg ggg cat ttt tac gaa ccc cag gct ccc tct gct        3725
Lys Ala Pro Val Gly His Phe Tyr Glu Pro Gln Ala Pro Ser Ala
1190                1195                1200 gag gtg gag atg aca tcc tat gtg ctc ctc gct tat ctc acg gcc        3770
Glu Val Glu Met Thr Ser Tyr Val Leu Leu Ala Tyr Leu Thr Ala
1205                1210                1215 cag cca gcc cca acc tcg gag gac ctg acc tct gca acc aac atc        3815
Gln Pro Ala Pro Thr Ser Glu Asp Leu Thr Ser Ala Thr Asn Ile
1220                1225                1230 gtg aag tgg atc acg aag cag cag aat gcc cag ggc ggt ttc tcc        3860
Val Lys Trp Ile Thr Lys Gln Gln Asn Ala Gln Gly Gly Phe Ser
1235                1240                1245 tcc acc cag gac aca gtg gtg gct ctc cat gct ctg tcc aaa tat        3905
Ser Thr Gln Asp Thr Val Val Ala Leu His Ala Leu Ser Lys Tyr
1250                1255                1260
```

```
gga gca gcc aca ttt acc agg act ggg aag gct gca cag gtg act      3950
Gly Ala Ala Thr Phe Thr Arg Thr Gly Lys Ala Ala Gln Val Thr
1265                1270                1275 atc cag tct tca ggg aca ttt tcc agc aaa ttc caa gtg gac aac      3995
Ile Gln Ser Ser Gly Thr Phe Ser Ser Lys Phe Gln Val Asp Asn
        1280                1285                1290 aac aac cgc ctg tta ctg cag cag gtc tca ttg cca gag ctg cct      4040
Asn Asn Arg Leu Leu Leu Gln Gln Val Ser Leu Pro Glu Leu Pro
1295                1300                1305 ggg gaa tac agc atg aaa gtg aca gga gaa gga tgt gtc tac ctc      4085
Gly Glu Tyr Ser Met Lys Val Thr Gly Glu Gly Cys Val Tyr Leu
1310                1315                1320 cag aca tcc ttg aaa tac aat att ctc cca gaa aag gaa gag ttc      4130
Gln Thr Ser Leu Lys Tyr Asn Ile Leu Pro Glu Lys Glu Glu Phe
1325                1330                1335 ttt gct tta gga gtg cag act ctg cct caa act tgt gat gaa          4175
Pro Phe Ala Leu Gly Val Gln Thr Leu Pro Gln Thr Cys Asp Glu
1340                1345                1350 ccc aaa gcc cac acc agc ttc caa atc tcc cta agt gtc agt tac      4220
Pro Lys Ala His Thr Ser Phe Gln Ile Ser Leu Ser Val Ser Tyr
1355                1360                1365 aca ggg agc cgc tct gcc tcc aac atg gcg atc gtt gat gtg aag      4265
Thr Gly Ser Arg Ser Ala Ser Asn Met Ala Ile Val Asp Val Lys
1370                1375                1380 atg gtc tct ggc ttc att ccc ctg aag cca aca gtg aaa atg ctt      4310
Met Val Ser Gly Phe Ile Pro Leu Lys Pro Thr Val Lys Met Leu
1385                1390                1395 gaa aga tct aac cat gtg agc cgg aca gaa gtc agc agc aac cat      4355
Glu Arg Ser Asn His Val Ser Arg Thr Glu Val Ser Ser Asn His
1400                1405                1410 gtc ttg att tac ctt gat aag gtg tca aat cag aca ctg agc ttg      4400
Val Leu Ile Tyr Leu Asp Lys Val Ser Asn Gln Thr Leu Ser Leu
1415                1420                1425 ttc ttc acg gtt ctg caa gat gtc cca gta aga gat ctg aaa cca      4445
Phe Phe Thr Val Leu Gln Asp Val Pro Val Arg Asp Leu Lys Pro
1430                1435                1440 gcc ata gtg aaa gtc tat gat tac tac gag acg gat gag ttt gca      4490
Ala Ile Val Lys Val Tyr Asp Tyr Tyr Glu Thr Asp Glu Phe Ala
1445                1450                1455 att gct gag tac aat gct cct tgc agc aaa gat ctt gga aat gct      4535
Ile Ala Glu Tyr Asn Ala Pro Cys Ser Lys Asp Leu Gly Asn Ala
1460                1465                1470 tgaagaccac aaggctgaaa agtgctttgc tggagtcctg ttctcagagc tccacagaag    4595
acacgtgttt ttgtatcttt aaagacttga tgaataaaca cttttctgg tcaatgtcaa    4655 aaaaaaaaaa aaaaaaaaaa aaa                                           4678

<210> SEQ ID NO 15
<211> LENGTH: 1474
<212> TYPE: PRT
<213> ORGANISM: Homo sapiens

<400> SEQUENCE: 15

Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
                20                  25                  30

Val Leu Val Pro Ser Leu Leu His Thr Glu Thr Thr Glu Lys Gly Cys
        35                  40                  45
```

-continued

```
Val Leu Leu Ser Tyr Leu Asn Glu Thr Val Thr Val Ser Ala Ser Leu
 50                  55                  60

Glu Ser Val Arg Gly Asn Arg Ser Leu Phe Thr Asp Leu Glu Ala Glu
 65                  70                  75                  80

Asn Asp Val Leu His Cys Val Ala Phe Ala Val Pro Lys Ser Ser Ser
                 85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
    290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
    355                 360                 365

Val Arg Leu Val Asp Gly Lys Gly Val Pro Ile Pro Asn Lys Val Ile
370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
    450                 455                 460

Ser His Glu Leu Pro Cys Gly His Thr Gln Thr Val Gln Ala His Tyr
```

```
              465                 470                 475                 480
      Ile Leu Asn Gly Gly Thr Leu Gly Leu Lys Lys Leu Ser Phe Tyr
                          485                 490                 495
      Tyr Leu Ile Met Ala Lys Gly Gly Ile Val Arg Thr Gly Thr His Gly
                          500                 505                 510
      Leu Leu Val Lys Gln Glu Asp Met Lys Gly His Phe Ser Ile Ser Ile
                          515                 520                 525
      Pro Val Lys Ser Asp Ile Ala Pro Val Ala Arg Leu Leu Ile Tyr Ala
                          530                 535                 540
      Val Leu Pro Thr Gly Asp Val Ile Gly Asp Ser Ala Lys Tyr Asp Val
      545                 550                 555                 560
      Glu Asn Cys Leu Ala Asn Lys Val Asp Leu Ser Phe Ser Pro Ser Gln
                          565                 570                 575
      Ser Leu Pro Ala Ser His Ala His Leu Arg Val Thr Ala Ala Pro Gln
                          580                 585                 590
      Ser Val Cys Ala Leu Arg Ala Val Asp Gln Ser Val Leu Leu Met Lys
                          595                 600                 605
      Pro Asp Ala Glu Leu Ser Ala Ser Ser Val Tyr Asn Leu Leu Pro Glu
                          610                 615                 620
      Lys Asp Leu Thr Gly Phe Pro Gly Pro Leu Asn Asp Gln Asp Asp Glu
      625                 630                 635                 640
      Asp Cys Ile Asn Arg His Asn Val Tyr Ile Asn Gly Ile Thr Tyr Thr
                          645                 650                 655
      Pro Val Ser Ser Thr Asn Glu Lys Asp Met Tyr Ser Phe Leu Glu Asp
                          660                 665                 670
      Met Gly Leu Lys Ala Phe Thr Asn Ser Lys Ile Arg Lys Pro Lys Met
                          675                 680                 685
      Cys Pro Gln Leu Gln Gln Tyr Glu Met His Gly Pro Glu Gly Leu Arg
                          690                 695                 700
      Val Gly Phe Tyr Glu Ser Asp Val Met Gly Arg Gly His Ala Arg Leu
      705                 710                 715                 720
      Val His Val Glu Glu Pro His Thr Glu Thr Val Arg Lys Tyr Phe Pro
                          725                 730                 735
      Glu Thr Trp Ile Trp Asp Leu Val Val Asn Ser Ala Gly Val Ala
                          740                 745                 750
      Glu Val Gly Val Thr Val Pro Asp Thr Ile Thr Glu Trp Lys Ala Gly
                          755                 760                 765
      Ala Phe Cys Leu Ser Glu Asp Ala Gly Leu Gly Ile Ser Ser Thr Ala
                          770                 775                 780
      Ser Leu Arg Ala Phe Gln Pro Phe Phe Val Glu Leu Thr Met Pro Tyr
      785                 790                 795                 800
      Ser Val Ile Arg Gly Glu Ala Phe Thr Leu Lys Ala Thr Val Leu Asn
                          805                 810                 815
      Tyr Leu Pro Lys Cys Ile Arg Val Ser Val Gln Leu Glu Ala Ser Pro
                          820                 825                 830
      Ala Phe Leu Ala Val Pro Val Glu Lys Glu Gln Ala Pro His Cys Ile
                          835                 840                 845
      Cys Ala Asn Gly Arg Gln Thr Val Ser Trp Ala Val Thr Pro Lys Ser
                          850                 855                 860
      Leu Gly Asn Val Asn Phe Thr Val Ser Ala Glu Ala Leu Glu Ser Gln
      865                 870                 875                 880
      Glu Leu Cys Gly Thr Glu Val Pro Ser Val Pro Glu His Gly Arg Lys
                          885                 890                 895
```

-continued

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Val Glu Glu Ser Ala
            930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
            995                 1000                1005

Asn Thr Gly Tyr Gln Arg Gln Leu Asn Tyr Lys His Tyr Asp Gly
        1010                1015                1020

Ser Tyr Ser Thr Phe Gly Glu Arg Tyr Gly Arg Asn Gln Gly Asn
        1025                1030                1035

Thr Trp Leu Thr Ala Phe Val Leu Lys Thr Phe Ala Gln Ala Arg
        1040                1045                1050

Ala Tyr Ile Phe Ile Asp Glu Ala His Ile Thr Gln Ala Leu Ile
        1055                1060                1065

Trp Leu Ser Gln Arg Gln Lys Asp Asn Gly Cys Phe Arg Ser Ser
        1070                1075                1080

Gly Ser Leu Leu Asn Asn Ala Ile Lys Gly Gly Val Glu Asp Glu
        1085                1090                1095

Val Thr Leu Ser Ala Tyr Ile Thr Ile Ala Leu Leu Glu Ile Pro
        1100                1105                1110

Leu Thr Val Thr His Pro Val Val Arg Asn Ala Leu Phe Cys Leu
        1115                1120                1125

Glu Ser Ala Trp Lys Thr Ala Gln Glu Gly Asp His Gly Ser His
        1130                1135                1140

Val Tyr Thr Lys Ala Leu Leu Ala Tyr Ala Phe Ala Leu Ala Gly
        1145                1150                1155

Asn Gln Asp Lys Arg Lys Glu Val Leu Lys Ser Leu Asn Glu Glu
        1160                1165                1170

Ala Val Lys Lys Asp Asn Ser Val His Trp Glu Arg Pro Gln Lys
        1175                1180                1185

Pro Lys Ala Pro Val Gly His Phe Tyr Glu Pro Gln Ala Pro Ser
        1190                1195                1200

Ala Glu Val Glu Met Thr Ser Tyr Val Leu Leu Ala Tyr Leu Thr
        1205                1210                1215

Ala Gln Pro Ala Pro Thr Ser Glu Asp Leu Thr Ser Ala Thr Asn
        1220                1225                1230

Ile Val Lys Trp Ile Thr Lys Gln Gln Asn Ala Gln Gly Gly Phe
        1235                1240                1245

Ser Ser Thr Gln Asp Thr Val Val Ala Leu His Ala Leu Ser Lys
        1250                1255                1260

Tyr Gly Ala Ala Thr Phe Thr Arg Thr Gly Lys Ala Ala Gln Val
        1265                1270                1275

Thr Ile Gln Ser Ser Gly Thr Phe Ser Ser Lys Phe Gln Val Asp
        1280                1285                1290

Asn Asn Asn Arg Leu Leu Leu Gln Gln Val Ser Leu Pro Glu Leu
    1295                1300                1305

Pro Gly Glu Tyr Ser Met Lys Val Thr Gly Glu Gly Cys Val Tyr
    1310                1315                1320

Leu Gln Thr Ser Leu Lys Tyr Asn Ile Leu Pro Glu Lys Glu Glu
    1325                1330                1335

Phe Pro Phe Ala Leu Gly Val Gln Thr Leu Pro Gln Thr Cys Asp
    1340                1345                1350

Glu Pro Lys Ala His Thr Ser Phe Gln Ile Ser Leu Ser Val Ser
    1355                1360                1365

Tyr Thr Gly Ser Arg Ser Ala Ser Asn Met Ala Ile Val Asp Val
    1370                1375                1380

Lys Met Val Ser Gly Phe Ile Pro Leu Lys Pro Thr Val Lys Met
    1385                1390                1395

Leu Glu Arg Ser Asn His Val Ser Arg Thr Glu Val Ser Ser Asn
    1400                1405                1410

His Val Leu Ile Tyr Leu Asp Lys Val Ser Asn Gln Thr Leu Ser
    1415                1420                1425

Leu Phe Phe Thr Val Leu Gln Asp Val Pro Val Arg Asp Leu Lys
    1430                1435                1440

Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala

<210> SEQ ID NO 16
<211> LENGTH: 55
<212> TYPE: DNA
<213> ORGANISM: Artificial
<220> FEATURE:
<223> OTHER INFORMATION: Synthetic polynucleotide

<400> SEQUENCE: 16
gctagcagac tacaaagacg atgacgacaa gtcagtctct ggaaaaccgc agtat          55

<210> SEQ ID NO 17
<211> LENGTH: 22
<212> TYPE: DNA
<213> ORGANISM: Artificial
<220> FEATURE:
<223> OTHER INFORMATION: Synthetic polynucleotide

<400> SEQUENCE: 17
cagtaagaga ggtacccata ac                                              22

<210> SEQ ID NO 18
<211> LENGTH: 22
<212> TYPE: DNA
<213> ORGANISM: Artificial
<220> FEATURE:
<223> OTHER INFORMATION: Synthetic polynucleotide

<400> SEQUENCE: 18
gttatgggta cctctcttac tg                                              22

<210> SEQ ID NO 19
<211> LENGTH: 20
<212> TYPE: DNA
<213> ORGANISM: Artificial

```
<220> FEATURE:
<223> OTHER INFORMATION: Synthetic polynucleotide

<400> SEQUENCE: 19
atgtaggctc gagcttgggc                                                  20

<210> SEQ ID NO 20
<211> LENGTH: 20
<212> TYPE: DNA
<213> ORGANISM: Artificial
<220> FEATURE:
<223> OTHER INFORMATION: Synthetic polynucleotide

<400> SEQUENCE: 20
gcccaagctc gagcctacat                                                  20

<210> SEQ ID NO 21
<211> LENGTH: 33
<212> TYPE: DNA
<213> ORGANISM: Artificial
<220> FEATURE:
<223> OTHER INFORMATION: Synthetic polynucleotide

<400> SEQUENCE: 21
gcggccgctc aagcatttcc aagatctttg ctg                                   33

<210> SEQ ID NO 22
<211> LENGTH: 23
<212> TYPE: DNA
<213> ORGANISM: Artificial
<220> FEATURE:
<223> OTHER INFORMATION: Synthetic polynucleotide

<400> SEQUENCE: 22
gatatgtaca gcttcctaga gga                                              23

<210> SEQ ID NO 23
<211> LENGTH: 32
<212> TYPE: DNA
<213> ORGANISM: Artificial
<220> FEATURE:
<223> OTHER INFORMATION: Synthetic polynucleotide

<400> SEQUENCE: 23
gttgcaattg tggacacatt ttgggtttac ga                                    32

<210> SEQ ID NO 24
<211> LENGTH: 34
<212> TYPE: DNA
<213> ORGANISM: Artificial
<220> FEATURE:
<223> OTHER INFORMATION: Synthetic polynucleotide

<400> SEQUENCE: 24
tccacaattg caacagtatg aaatgcatgg acct                                  34

<210> SEQ ID NO 25
<211> LENGTH: 22
<212> TYPE: DNA
<213> ORGANISM: Artificial
<220> FEATURE:
<223> OTHER INFORMATION: Synthetic polynucleotide

<400> SEQUENCE: 25
ctttcgtacg gtctccgtgt ga                                               22
```

```
<210> SEQ ID NO 26
<211> LENGTH: 30
<212> TYPE: DNA
<213> ORGANISM: Artificial
<220> FEATURE:
<223> OTHER INFORMATION: Synthetic polynucleotide

<400> SEQUENCE: 26
gagagaattc tgggacttca ccctggacga                                30

<210> SEQ ID NO 27
<211> LENGTH: 30
<212> TYPE: DNA
<213> ORGANISM: Artificial
<220> FEATURE:
<223> OTHER INFORMATION: Synthetic polynucleotide

<400> SEQUENCE: 27
gaaaggtacc atggcgctgt aggtgggtgt                                30

<210> SEQ ID NO 28
<211> LENGTH: 10
<212> TYPE: PRT
<213> ORGANISM: Artificial
<220> FEATURE:
<223> OTHER INFORMATION: Synthetic polypeptide

<400> SEQUENCE: 28

Ser Val Ser Gly Lys Pro Gln Tyr Met Val
1               5                   10

<210> SEQ ID NO 29
<211> LENGTH: 9
<212> TYPE: PRT
<213> ORGANISM: Artificial
<220> FEATURE:
<223> OTHER INFORMATION: Synthetic polypeptide
<220> FEATURE:
<221> NAME/KEY: UNSURE
<222> LOCATION: (8)..(8)
<223> OTHER INFORMATION: X is an unidentified residue.

<400> SEQUENCE: 29

Asp Val Met Gly Arg Gly His Xaa Arg
1               5
```